(12) United States Patent
Sommazzi et al.

(10) Patent No.: US 10,954,326 B2
(45) Date of Patent: *Mar. 23, 2021

(54) PROCESS FOR THE PREPARATION OF SYNDIOTACTIC 1,2-POLYBUTADIENE IN THE PRESENCE OF A CATALYTIC SYSTEM COMPRISING A PYRIDYL IRON COMPLEX

(71) Applicant: Versalis S.P.A., San Donato Milanese (IT)

(72) Inventors: Anna Sommazzi, Novara (IT); Guido Pampaloni, Pontedera (IT); Giovanni Ricci, Parma (IT); Francesco Masi, Sant'Angelo Lodigiano (IT); Giuseppe Leone, Milan (IT)

(73) Assignee: Versalis S.P.A., San Donato Milanese (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/341,142

(22) PCT Filed: Oct. 20, 2017

(86) PCT No.: PCT/IB2017/056528
§ 371 (c)(1),
(2) Date: Apr. 11, 2019

(87) PCT Pub. No.: WO2018/073798
PCT Pub. Date: Apr. 26, 2018

(65) Prior Publication Data
US 2020/0024379 A1  Jan. 23, 2020

(30) Foreign Application Priority Data
Oct. 20, 2016 (IT) .................. IT102016000105530

(51) Int. Cl.
| | |
|---|---|
| C08F 4/52 | (2006.01) |
| C08F 136/06 | (2006.01) |
| A43B 13/04 | (2006.01) |
| C08F 4/70 | (2006.01) |
| C08F 4/80 | (2006.01) |
| C07C 251/02 | (2006.01) |

(52) U.S. Cl.
CPC ............ *C08F 136/06* (2013.01); *A43B 13/04* (2013.01); *C08F 4/52* (2013.01); *C08F 4/7006* (2013.01); *C08F 4/80* (2013.01); *C07C 251/02* (2013.01)

(58) Field of Classification Search
CPC ........... C08F 36/04; C08F 4/80; C07C 251/02
See application file for complete search history.

(56) References Cited

U.S. PATENT DOCUMENTS

| | | |
|---|---|---|
| 3,966,697 A | 6/1976 | Kampf et al. |
| 3,983,183 A | 9/1976 | Kampf |
| 4,176,219 A | 11/1979 | Makino et al. |
| 4,182,813 A | 1/1980 | Makino et al. |
| 4,463,146 A | 7/1984 | Donbar et al. |
| 5,548,045 A | 8/1996 | Goto et al. |
| 5,986,026 A | 11/1999 | Wong et al. |
| 6,160,063 A | 12/2000 | Luo |
| 6,180,734 B1 | 1/2001 | Luo |
| 6,211,313 B1 | 4/2001 | Luo |
| 6,277,779 B1 | 8/2001 | Luo |
| 6,284,702 B1 | 9/2001 | Luo |
| 6,388,030 B2 | 5/2002 | Luo et al. |
| 6,479,601 B1 * | 11/2002 | Kerns ............... C08F 36/04 502/155 |

(Continued)

FOREIGN PATENT DOCUMENTS

| | | |
|---|---|---|
| JP | 2004/107617 A | 4/2004 |
| JP | 2005/008836 A | 1/2005 |
| WO | WO 02/102861 A2 | 12/2002 |
| WO | WO 2004020413 * | 8/2003 |
| WO | WO 2011/061151 A1 | 5/2011 |

(Continued)

OTHER PUBLICATIONS

USPTO structure search, Oct. 2020.*
Office Action issued by Russian Patent Office for Application No. 201990454/28 dated Dec. 20, 2019, 2 pages. Translation in English provided.

(Continued)

*Primary Examiner* — Gregory Listvoyb
(74) *Attorney, Agent, or Firm* — Praedcere Law

(57) ABSTRACT

Process for the preparation of syndiotactic 1,2-polybutadiene comprising polymerising 1,3-butadiene in the presence of a catalytic system comprising: —at least one pyridyl iron complex having the general formula (I), in which: —$R_1$ represents a hydrogen atom; or a methyl group; —$R_2$ represents a hydrogen atom; or is selected from linear or branched $C_1$-$C_{10}$ alkyl groups; —X, identical or different to one another, represent a halogen atom; or are selected from linear or branched, $C_1$-$C_{20}$ alkyl groups, —$OCOR_3$ groups or —$OR_3$ groups in which $R_3$ is selected from linear or branched $C_1$-$C_{20}$ alkyl groups; —n is 2 or 3; —at least one aluminoxane having the general formula (II), $(R_4)_2$-Al-O-[-Al($R_5$)—O-]$_m$-Al-($R_6$)$_2$ (II) in which $R_4$, $R_5$ and $R_6$, identical or different to one another, represent a hydrogen atom, or a halogen atom; or are selected from linear or branched $C_1$-$C_{20}$ alkyl groups, cycloalkyi groups, aryl groups, said groups being optionally substituted with one or more silicon atoms or germanium; and m is an integer ranging from 0 to 1000; in which the molar ratio between the aluminium present in the aluminoxane having the general formula (II) and the iron present in the pyridyl iron complex having the general formula (I) is ranging from 5 to 20.

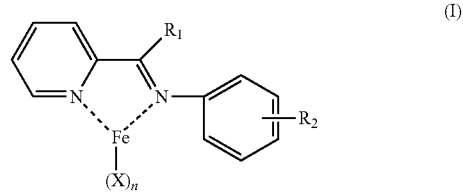

(I)

6 Claims, 28 Drawing Sheets

(56) References Cited

U.S. PATENT DOCUMENTS

| | | | |
|---|---|---|---|
| 2001/0036899 A1 | 11/2001 | Luo et al. | |
| 2002/0013435 A1 | 1/2002 | Luo et al. | |
| 2003/0073790 A1 | 4/2003 | Luo et al. | |
| 2014/0011971 A1* | 1/2014 | Ritter | C08F 36/08 526/172 |
| 2015/0329654 A1 | 11/2015 | Masi et al. | |
| 2016/0264706 A1 | 9/2016 | Masi et al. | |

FOREIGN PATENT DOCUMENTS

| | | |
|---|---|---|
| WO | WO 2012/109343 A2 | 8/2012 |
| WO | WO20160142014 A1 | 3/2016 |
| WO | WO 2016/042014 A1 | 3/2016 |

OTHER PUBLICATIONS

International Search Report & Written Opinion for PCT/IB2017/056528, 9 pages.

Takeuchi et al., "New Industrial Polymers", "American Chemical Society Symposium Series" (1974), vol. 4, pp. 15-25.

Halasa et al., "Kirk-Othmer Encyclopedia of Chemical Technology" (1989), 4th ed., Kroschwitz J. I. ed., John Wiley and Sons, New York, vol. 8, pp. 1031-1045.

Tate et al., Encyclopedia of Polymer Science and Engineering (1989), 2nd ed., Mark H. F. ed., John Wiley and Sons, New York, vol. 2, pp. 537-590.

Kerns et al., "Butadiene Polymers", in "Encyclopedia of Polymer Science and Technology" (2003), Mark H. F. ed., Wiley, vol. 5, pp. 317-356.

Porri et al., "Comprehensive Polymer Science" (1989), Eastmond G.C. et al. eds., Pergamon Press, Oxford, UK, vol. 4, part II, pp. 53-108.

Thiele et al., "Macromolecular Science. Part C: Polymer Reviews" (2003), C43, pp. 581-628.

Osakada et al., "Advanced Polymer Science" (2004), vol. 171, pp. 137-194.

Friebe et al., "Advanced Polymer Science" (2006), vol. 204, pp. 1-154.

Zhang et al., "Journal of Molecular Catalysis" (1982), vol. 17, issue 1, pp. 65-76.

Bazzini et al., "Macromolecular Rapid Communications" (2002), vol. 23(15), pp. 922-927.

Bazzini et al., "Polymer Communication" (2004), vol. 45, pp. 2871-2875.

Ricci et al., "Journal of Molecular Catalysis A: Chemical" (2003), vol. 204-205, pp. 287-293.

Ricci et al., "Coordination Chemistry Reviews" (2010), vol. 254, issues 5-6, pp. 661-676.

Nakayama et al., "Macromolecules" (2003), vol. 36(21), pp. 7953-7958.

Gong et al., "Polymer" (2009), vol. 50, pp. 5980-5986.

Gong et al., "Polymer" (2009), vol. 50, pp. 6259-6264.

Gong et al., "Inorganic Chimica Acta" (2011), vol. 373, issue 1, pp. 47-53.

Gong et al., "Journal of Organometallic Chemistry" (2012), vol. 702, pp. 10-18.

Zhang et al., "Dalton Transactions" (2012), vol. 41, pp. 9639-9645.

Raynaud et al., "Angewandte Chemie International Edition" (2012), vol. 51, pp. 11805-11808.

Wang et al., "Polymer" (2013), vol. 54, pp. 5174-5181.

Liu et al., "Journal of Molecular Catalysis A: Chemical" (2014), vol. 391, pp. 25-35.

Gong et al., "Journal of Molecular Catalysis A: Chemical" (2015), vol. 406, pp. 78-84.

Zheng et al., "Journal of Polymer Science Part A: Polymer Chemistry" (2015), vol. 53, issue 10, pp. 1182-1188.

Wu et al., "Journal of American Chemical Society" (2009), vol. 131(36), pp. 12915-12917.

Laine et al., "European Journal of Inorganic Chemistry" (1999), vol. 6, pp. 959-964.

Bianchini et al., "New Journal of Chemistry" (2002), vol. 26(4), pp. 387-397.

Lai et al., "Tetrahedron" (2005), vol. 61(40), pp. 9484-9489.

Ricci et al., "Advances in Organometallic Chemistry Research" (2007), Yamamoto K. ed., Nova Science Publisher, Inc., USA, pp. 1-36.

Ricci et al., "Coordination Chemistry Reviews" (2010), vol. 254, pp. 661-676.

Ricci et al., "Ferrocenes: Compounds, Properties and Applications" (2011), Elisabeth S. Phillips ed., Nova Science Publisher, Inc., USA, pp. 273-313.

Ricci et al., "Chromium: Environmental, Medical and Material Studies" (2011), Margaret P. Salden ed., Nova Science Publisher, Inc., USA, pp. 121-1406.

Ricci et al., "Cobalt: Characteristics, Compounds, and Applications" (2011), Lucas J. Vidmar ed., Nova Science Publisher, Inc., USA, pp. 39-81.

Ricci et al., "Phosphorus: Properties, Health effects and Environment" (2012), Ming Yue Chen and Da-Xia Yang eds., Nova Science Publisher, Inc., USA, pp. 53-94.

Cotton et al., in "Inorganic Chimica Acta" (1991), vol. 179, pp. 11-15.

Mochel, in "Journal of Polymer Science Part A-1: Polymer Chemistry" (1972), vol. 10, issue 4, pp. 1009-1018.

\* cited by examiner

G1525

PROCESS FOR THE PREPARATION OF SYNDIOTACTIC 1,2-POLYBUTADIENE IN THE PRESENCE OF A CATALYTIC SYSTEM COMPRISING A PYRIDYL IRON COMPLEX

The present invention relates to a process for the preparation of syndiotactic 1,2-polybutadiene.

More particularly, the present invention relates to a process for the preparation of syndiotactic 1,2-polybutadiene comprising polymerising 1,3-butadiene in the presence of a catalytic system comprising: at least one pyridyl iron complex; at least one aluminoxane. Stereospecific (co)polymerisation of conjugated dienes is known to be a very important process in the chemicals industry for obtaining products which are among the most widely used rubbers.

It is also known that, among the various polymers obtainable by the stereospecific polymerisation of 1,3-butadiene (i.e. 1,4-cis, 1,4-trans, 1,2-syndiotactic, 1,2-isotactic, 1,2-atactic, 1,4-cis/1,2 mixed structure having a variable content of 1,2 units), only 1,4-cis polybutadiene and syndiotactic 1,2-polybutadiene are produced industrially and commercialized. Further details relating to said polymers may be found, for example, in: Takeuchi Y. et al., "*New Industrial Polymers*", "*American Chemical Society Symposium Series*" (1974), vol. 4, pp. 15-25; Halasa A. F. et al., "*Kirk-Othmer Encyclopedia of Chemical Technology*" (1989), 4$^{th}$ ed., Kroschwitz J. I. ed., John Wiley and Sons, New York, vol. 8, pp. 1031-1045; Tate D. et al., "*Encyclopedia of Polymer Science and Engineering* (1989), 2$^{nd}$ ed., Mark H. F. ed., John Wiley and Sons, New York, vol. 2, pp. 537-590; Kerns M. et al., "*Butadiene Polymers*", in "*Encyclopedia of Polymer Science and Technology*" (2003), Mark H. F. ed., Wiley, vol. 5, pp. 317-356.

Generally, 1,4-cis polybutadiene is prepared by polymerisation processes which make use of various catalytic systems comprising catalysts based on titanium (Ti), cobalt (Co), nickel (Ni), neodymium (Nd). Catalytic systems comprising catalysts based on cobalt exhibit high catalytic activity and stereospecificity and may be considered the most versatile among those mentioned above given that, by varying the formulation thereof, they are capable of yielding all the possible stereoisomers of polybutadiene mentioned above, as described, for example, in: Porri L. et al., "*Comprehensive Polymer Science*" (1989), Eastmond G. C. et al. eds., Pergamon Press, Oxford, UK, vol. 4, part II, pp. 53-108; Thiele S. K. H. et al., "*Macromolecular Science. Part C: Polymer Reviews*" (2003), C43, pp. 581-628; Osakada, K. et al., "*Advanced Polymer Science*" (2004), vol. 171, pp. 137-194; Friebe L. et al., "*Advanced Polymer Science*" (2006), vol. 204, pp. 1-154.

Catalytic systems comprising catalysts based on cobalt and phosphorus compounds (for example, aryl- or alkyl-phosphines) capable of yielding syndiotactic 1,2-polybutadiene are described, for example, in American patents U.S. Pat. Nos. 3,966,697, 3,983,183, 4,176,219, 4,182,813, 4,463,146, 5,548,045, 5,986,026; Japanese patent applications JP 2004/107617, JP 2005/008836.

Catalysts based on iron (Fe) usable in the (co)polymerisation of conjugated dienes have also been investigated. One of the first studies mentioned in the literature relating to catalytic systems comprising catalysts based on iron (Fe) concerned the (co)polymerisation of 1,3-butadiene and isoprene with catalytic systems comprising iron acetylacetonate [Fe(acac)$_3$], tri-iso-butylaluminium (TIBA) and 1,10-phenanthroline (phen) as described, for example, in Zhang Z. Y. et al., "*Journal of Molecular Catalysis*" (1982), vol. 17, issue 1, pp. 65-76. Said catalytic system is capable of yielding a binary polybutadiene with a mixed 1,4-cis/1,2 structure having an equal content of 1,4-cis and 1,2 units.

American patent U.S. Pat. No. 6,160,063 describes a catalytic system obtained by combining or reacting: a compound containing iron (for example, iron carboxylate, iron β-diketonate, iron alkoxide, iron arylalkoxide); an organic magnesium compound; and a cyclic hydrogen phosphite. The above-stated catalytic system is particularly useful for polymerising 1,3-butadiene to yield binary polybutadiene with a mixed 1,4-cis/1,2 structure.

American patent U.S. Pat. No. 6,180,734 describes a catalytic system obtained by combining or reacting: a compound containing iron (for example, iron carboxylate, iron β-diketonate, iron alkoxide, iron arylalkoxide); a cyclic hydrogen phosphite; and an organic aluminium compound. The above-stated catalytic system is particularly useful for polymerising 1,3-butadiene to yield syndiotactic 1,2-polybutadiene.

American patent U.S. Pat. No. 6,211,313 describes a catalytic system obtained by combining or reacting: a compound containing iron (for example, iron carboxylate, iron β-diketonate, iron alkoxide, iron arylalkoxide); a cyclic hydrogen phosphite; and an aluminoxane. The above-stated catalytic system is particularly useful for polymerising 1,3-butadiene to yield syndiotactic 1,2-polybutadiene.

American patent U.S. Pat. No. 6,277,779 describes a catalytic system obtained by combining or reacting: a compound containing iron (for example, iron carboxylate, iron β-diketonate, iron alkoxide, iron arylalkoxide); a cyclic hydrogen phosphite; and an organic aluminium compound. The above-stated catalytic system is particularly useful for polymerising 1,3-butadiene to yield syndiotactic 1,2-polybutadiene having a melting temperature which may vary from 100° C. to 200° C., depending on the components of and the ratios between the various components present in said catalytic system.

American patents U.S. Pat. Nos. 6,284,702 and 6,388,030 describe a catalytic system obtained by combining or reacting: a compound containing iron (for example, iron carboxylate, iron β-diketonate, iron alkoxide, iron arylalkoxide); an organic magnesium compound; and a dihydrocarbyl hydrogen phosphite. The above-stated catalytic system is particularly useful for polymerising 1,3-butadiene to yield syndiotactic 1,2-polybutadiene having a melting temperature which may vary from 100° C. to 190° C., depending on the components of and the ratios between the various components present in said catalytic system.

Catalytic systems comprising, for example, iron diethyl-bis(2,2'-bipyridine) [FeEt$_2$(bipy)$_2$] and methylaluminoxane (MAO), or comprising various complexes of iron dichloride (FeCl$_2$) with bidentate aromatic amines (for example, N,N,N',N'-tetramethylethylenediamine (TMEDA), N,N'-dimethylethylenediamine (DMEDA), 2,2'-bipyridine (bipy), 1,10-phenanthroline (phen), and compounds of aluminium [for example, alkylaluminiums (AlR$_3$ in which R is ethyl or iso-butyl), methylaluminoxane (MAO)], are extremely active in the (co)polymerisation of conjugated dienes, as described, for example, in international patent application WO 02/102861; or in Bazzini C. et al., "*Macromolecular Rapid Communications*" (2002), vol. 23(15), pp. 922-927; Bazzini C. et al., "*Polymer Communication*" (2004), vol. 45, pp. 2871-2875; Ricci G. et al., "*Journal of Molecular Catalysis A: Chemical*" (2003), vol. 204-205, pp. 287-293; Ricci G. et al., "*Coordination Chemistry Reviews*" (2010), vol. 254, issues 5-6, pp. 661-676. Such catalytic systems are capable of yielding polybutadienes with a predominantly 1,2 structure: in particular, the polybutadienes obtained at low temperature exhibit a 1,2 structure of approx. 90% and a content of syndiotactic pentads of 50%, and the content of 1,2 units and syndiotactic pentads decreases as polymerisation temperature rises. Furthermore, the polybutadienes obtained with the above-stated catalytic systems have a very high weight-average molecular weight ($M_w$) and a polydispersity index (PDI) corresponding to the ratio $M_w/M_n$ ($M_n$=number-average molecular weight) which is rather low, e.g., in the range of from 1 to 2, to indicate a "pseudo-living" nature of said catalytic systems which are stated to be "single site". The nature of the amino ligand has also been observed to have an appreciable effect on the catalytic activity of said catalytic systems: in particular, catalytic activity decreases as the steric hindrance of the ligand increases. Furthermore, the type of aluminium compound may also have an impact on catalytic activity: indeed, it has been observed that using methylaluminoxane (MAO) results in an increase in 1,2 unit content under identical polymerisation conditions. The above-stated catalytic systems have, furthermore, also proved to be extremely active and selective not only in the polymerisation of 1,3-butadiene but also in the (co)polymerisation of other conjugated dienes such as, for example, isoprene, 2,3-dimethyl-1,3-butadiene, 3-methyl-1,3-pentadiene, yielding (co)polymers having different structures such as, for example, syndiotactic 3,4-polyisoprene, 1,4-cis-poly(2,3-dimethyl-1,3-butadiene) or syndiotactic E-1,2-poly(3-methyl-1,3-pentadiene).

Catalytic systems comprising ter-pyridyl iron complexes [for example, $FeCl_3$(ter-pyridine)], in combination with appropriate alkylating agents, are useful in the stereospecific polymerisation of conjugated dienes: said catalytic systems exhibit a moderate catalytic activity and are capable of yielding polybutadienes with a 1,4-trans structure as described, for example, in Nakayama Y. et al., "*Macromolecules*" (2003), vol. 36(21), pp. 7953-7958. Catalytic systems obtained by combining iron(III) carboxylates (for example, iron(III) 2-ethylhexanoate [Fe(2-EHA)$_3$]Fe(III) with tri-iso-butylaluminium (Al$^i$Bu$_3$) in hexane, in the presence of phosphates (for example, triethylphosphate) are capable of polymerising 1,3-butadiene to form polybutadiene with a predominantly 1,2 structure and with a high level of syndiotacticity as described, for example, in Gong D. et al., "*Polymer*" (2009), vol. 50, pp. 5980-5986.

Catalytic systems comprising complexes obtained from iron trichloride ($FeCl_3$) or from iron dichloride tetrahydrate ($FeCl_2 \cdot 4H_2O$) with 2,6-bis[1-(iminophenyl)ethyl]pyridine or substituted 2,6-bis(imino)pyridines, in the presence of methylaluminoxane (MAO), are capable of yielding polybutadienes with a high content (>90%) of 1,4-trans structures, or a mixed 1,4-cis/1,4-trans structure, as a function of the catalytic system used, as described, for example, in: Gong D. et al., "*Polymer*" (2009), vol. 50, pp. 6259-6264; Gong D. et al., "*Inorganic Chimica Acta*" (2011), vol. 373, issue 1, pp. 47-53.

Catalytic systems comprising complexes obtained from iron trichloride ($FeCl_3$) or from iron dichloride tetrahydrate ($FeCl_2 \cdot 4H_2O$) with substituted 2,6-bis[1-(2-benzoimidazolyl)]pyridines or substituted 2,6-bis(pyrazolyl)pyridines in the presence of modified methylaluminoxane (MMAO) or diethylaluminium chloride (AlEt$_2$Cl), are capable of yielding polybutadienes with various structures, namely 1,4-trans or 1,4-cis, as a function of the catalytic system used, as described, for example, in Gong D. et al., "*Journal of Organometallic Chemistry*" (2012), vol. 702, pp. 10-18.

Bis-imino pincer complexes of iron(II) [Fe(II)] in combination with alkylaluminium [for example, trimethylaluminium (AlMe$_3$)] are capable of yielding polybutadiene with a substantially 1,4-cis structure (≥70%) as described, for example, in Zhang J. et al., "*Dalton Transactions*" (2012), vol. 41, pp. 9639-9645.

Catalytic systems comprising iminopyridyl complexes of iron(II), alkylaluminiums (for example, AlR$_3$ in which R is ethyl or iso-butyl), and boron salts, are capable of polymerising isoprene to yield polyisoprene with a high 1,4-trans structure content as described, for example, in Raynaud J. et al., "*Angewandte Chemie International Edition*" (2012), vol. 51, pp. 11805-11808; or in international patent application WO 2012/109343. Catalytic systems comprising complexes of iron(II) with substituted 1,10-phenanthroline-2-pyrazolyl and alkylaluminiums (for example, AlR$_3$ in which R is ethyl, iso-butyl, octyl), are characterised by high catalytic activity and selectivity and are capable of yielding polybutadienes with a 1,4-trans structure content as described, for example, in Wang B. et al., "*Polymer*" (2013), vol. 54, pp. 5174-5181.

Catalytic systems comprising complexes of iron(II) with 2-(N-arylcarboxyimidoylchloride)quinoline and alkylaluminiums [for example, AlR$_3$ in which R is ethyl, iso-butyl; or methylaluminoxane (MAO)], are characterised by low catalytic activity and are capable of yielding polybutadienes with a high 1,4-cis structure content as described, for example, in Liu H. et al., "*Journal of Molecular Catalysis A: Chemical*" (2014), vol. 391, pp. 25-35.

Catalytic systems comprising complexes of iron(II) with 2,6-bis(dimethyl-2-oxazolin-2-yl)pyridine and alkylaluminiums [for example, AlR$_3$ in which R is ethyl, iso-butyl; or methylaluminoxane (MAO)], are capable of yielding polybutadiene with a mixed 1,4-cis/1,4-trans structure as described, for example, in Gong D. et al., "*Journal of Molecular Catalysis A: Chemical*" (2015), vol. 406, pp. 78-84.

Finally, polybutadienes with "soft/hard" stereoblocks with a mixed 1,4-cis/1,2 structure have been obtained using the catalytic system iron 2-ethylhexanoate/tri-iso-butylaluminium/diethyl phosphate [Fe(2-EHA)$_3$/Al$^i$Bu$_3$/DEP], by appropriately varying the aluminium/iron (Al/Fe) ratio as described, for example, in Zheng W. et al., "*Journal of Polymer Science Part A: Polymer Chemistry*" (2015), vol. 53, issue 10, pp. 1182-1188. Since syndiotactic 1,2-polybutadiene may be advantageously used in various sectors such as, for example, in the footwear industry, in particular in the production of shoe soles, there is still great interest in investigating new processes capable of providing said polybutadiene.

The Applicant has faced the problem of finding a new process capable of yielding syndiotactic 1,2-polybutadiene.

The Applicant has now found a process for the preparation of syndiotactic 1,2-polybutadiene comprising polymerising 1,3-butadiene in the presence of a catalytic system comprising: at least one pyridyl iron complex having the specific general formula (I) shown below; at least one aluminoxane. Using said catalytic system makes it possible to obtain a syndiotactic 1,2-polybutadiene having a 1,2 unit content of greater than or equal to 60% and a content of syndiotactic triads (rr %) of greater than or equal to 50%. Said catalytic system, furthermore, makes it possible to operate at a low molar ratio between the aluminium present in the aluminoxane and the iron present in the pyridyl iron complex having the specific general formula (I) shown below and, in particular, thanks to its high catalytic activity, to use small quantities of aluminoxane and iron, with consequent appreciable advantages from an economic standpoint. Furthermore, said catalytic system may be used in the presence of an inert organic solvent selected from aliphatic hydrocarbons, with consequent appreciable advantages from both an economic and an environmental standpoint.

The present invention accordingly provides a process for the preparation of syndiotactic 1,2-polybutadiene comprising polymerising 1,3-butadiene in the presence of a catalytic system comprising:

at least one pyridyl iron complex having the general formula (I):

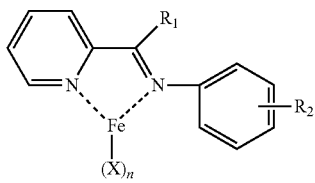

in which:
- $R_1$ represents a hydrogen atom; or a methyl group;
- $R_2$ represents a hydrogen atom; or is selected from linear or branched $C_1$-$C_{10}$, preferably $C_1$-$C_3$, alkyl groups;
- X, identical or different to one another, represent a halogen atom such as, for example, chlorine, bromine or iodine; or are selected from linear or branched, $C_1$-$C_{20}$, preferably $C_1$-$C_{15}$, alkyl groups, —OCOR$_3$ groups or —OR$_3$ groups in which $R_3$ is selected from linear or branched $C_1$-$C_{20}$, preferably $C_1$-$C_{15}$, alkyl groups;
- n is 2 or 3;

at least one aluminoxane having the general formula (II):

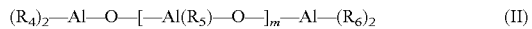

$$(R_4)_2\text{—Al—O—}[\text{—Al}(R_5)\text{—O—}]_m\text{—Al—}(R_6)_2 \quad (II)$$

in which $R_4$, $R_5$ and $R_6$, identical or different to one another, represent a hydrogen atom, or a halogen atom such as, for example, chlorine, bromine, iodine or fluorine; or are selected from linear or branched $C_1$-$C_{20}$ alkyl groups, cycloalkyl groups, aryl groups, said groups being optionally substituted with one or more silicon atoms or germanium; and m is an integer ranging from 0 to 1000;

in which the molar ratio between the aluminium present in the aluminoxane having the general formula (II) and the iron present in the pyridyl iron complex having the general formula (I) is ranging from 5 to 20, preferably ranging from 8 to 12.

For the purpose of the present description and of the following claims, unless stated otherwise, definitions of numerical ranges always include the extremes.

For the purpose of the present description and of the following claims, the term "comprising" also encompasses the terms "which essentially consists of" or "which consists of".

For the purpose of the present description and of the following claims, the terms "$C_1$-$C_{10}$ alkyl groups" and "$C_1$-$C_{20}$ alkyl groups" are taken to mean linear or branched alkyl groups respectively having from 1 to 10 carbon atoms and from 1 to 20 carbon atoms. Specific examples of $C_1$-$C_{10}$ and $C_1$-$C_{20}$ alkyl groups are: methyl, ethyl, n-propyl, iso-propyl, n-butyl, s-butyl, iso-butyl, tert-butyl, pentyl, hexyl, heptyl, octyl, n-nonyl, n-decyl, 2-butyloctyl, 5-methylhexyl, 4-ethylhexyl, 2-ethylheptyl, 2-ethylhexyl.

For the purpose of the present description and of the following claims, the term "cycloalkyl groups" is taken to mean cycloalkyl groups having from 3 to 30 carbon atoms. Said cycloalkyl groups may optionally also be substituted with one or more groups identical or different to one another selected from: halogen atoms; hydroxyl groups; $C_1$-$C_{12}$ alkyl groups; $C_1$-$C_{12}$ alkoxy groups; cyano groups; amino groups; nitro groups. Specific examples of cycloalkyl groups are: cyclopropyl, 2,2-difluorocyclopropyl, cyclobutyl, cyclopentyl, cyclohexyl, hexamethylcyclohexyl, pentamethylcyclopentyl, 2-cyclooctylethyl, methylcyclohexyl, methoxycyclohexyl, fluorocyclohexyl, phenylcyclohexyl.

For the purpose of the present description and of the following claims, the term "aryl groups" are taken to mean aromatic carbocyclic groups. Said aryl groups may optionally also be substituted with one or more groups identical or different to one another selected from: halogen atoms such as, for example, fluorine, chlorine, bromine; hydroxyl groups; $C_1$-$C_{12}$ alkyl groups; $C_1$-$C_{12}$ alkoxy groups; cyano groups; amino groups; nitro groups. Specific examples of aryl groups are: phenyl, 2-methylphenyl, 4-methylphenyl, 2-tert-butylphenyl, 2,4,6-trimethylphenyl, 2-iso-propylphenyl, 2,6-di-iso-propylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

According to a preferred embodiment of the present invention, in said pyridyl iron complex having the general formula (I):
- $R_1$ represents a hydrogen atom; or a methyl group;
- $R_2$ represents a hydrogen atom; or a methyl group, an ethyl group, an n-propyl group, an iso-propyl group, preferably a methyl group or an iso-propyl group;
- X, identical to one another, represent a halogen atom such as, for example, chlorine, bromine, iodine; preferably represent a chlorine atom;
- n is 2 or 3.

The pyridyl iron complex having the general formula (I) should be understood in accordance with the present invention to have any physical form such as, for example, an isolated and purified solid form, a form solvated with an appropriate solvent, or that supported on suitable organic or inorganic solids, preferably having a granular or pulverulent physical form.

The pyridyl iron complex having the general formula (I) is prepared starting from ligands known in the art.

Specific examples of ligands usable for the purposes of the present invention are those having the following formulae (L1), (L2) and (L3):

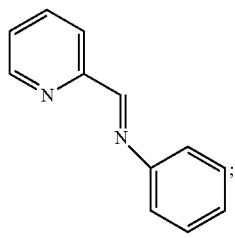

(L1)

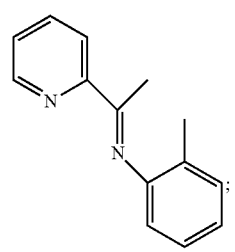

(L2)

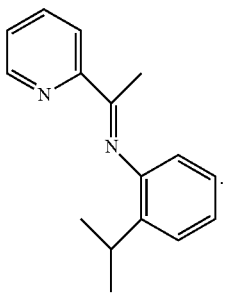

(L3)

Said ligands having the formulae (L1), (L2) and (L3), may be prepared by way of processes known in the art. For example, said ligands having the formulae (L1), (L2) and (L3) may be prepared by a process comprising: (1) condensation reactions between an appropriate aniline and 2-pyridinecarboxaldehyde or 2-acetylpyridine, with formation of the corresponding imine as described, for example, in: Wu J. et al., "*Journal of American Chemical Society*" (2009), vol. 131(36), pp. 12915-12917; Laine V. T. et al., "*European Journal of Inorganic Chemistry*" (1999), vol. 6, pp. 959-964; Bianchini C. et al., "*New Journal of Chemistry*" (2002), vol. 26(4), pp. 387-397; Lai Yi-C. et al., "*Tetrahedron*" (2005), vol. 61(40), pp. 9484-9489.

The pyridyl iron complex having the general formula (I) may be prepared in accordance with processes known in the art. For example, said pyridyl iron complex may be prepared by reaction between iron compounds having the general formula $Fe(X)_2$ or $Fe(X)_3$ in which X is a halogen atom such as, for example, chlorine, bromine, iodine, preferably chlorine, as such or complexed with ethers [for example, diethyl ether, tetrahydrofuran (THF), dimethoxyethane] or with water, with appropriate pyridyl ligands (L), such as, for example, the above-mentioned ligands having the formulae (L1), (L2) or (L3), in a molar ratio of ligand (L):iron (Fe) of from 1 to 2, preferably working in the presence of at least one solvent which may be selected, for example, from: chlorinated solvents (for example, methylene chloride), ether solvents [for example, tetrahydrofuran (THF)], alcohol solvents (for example, butanol), hydrocarbon solvents (for example, toluene) or mixtures thereof, at a temperature ranging from room temperature to 110° C. The pyridyl iron complex having the general formula (I) obtained in this manner may subsequently be recovered by known prior art methods such as, for example, washing the solid product obtained with an appropriate solvent (for example, heptane), followed by drying (for example, under vacuum). Further details relating to the process for the preparation of said pyridyl iron complex having the general formula (I) may be found in the following examples.

For the purpose of the present description and of the following claims, the phrase "room temperature" is taken to mean a temperature of ranging from 20° C. to 25° C.

As is known, aluminoxanes are compounds containing Al—O—Al bonds, with a variable O/Al ratio, which are obtainable according to processes known in the art such as, for example, by reaction, under controlled conditions, of an alkylaluminium or an alkylaluminium halide, with water or with other compounds containing predetermined quantities of available water, such as, for example, in the case of the reaction of trimethylaluminium with aluminium sulfate hexahydrate, copper sulfate pentahydrate or iron sulfate pentahydrate. Said aluminoxanes and, in particular, methylaluminoxane (MAO), are compounds obtainable by means of known processes of organometallic chemistry such as, for example, by addition of trimethylaluminium to a suspension of aluminium sulfate hydrate in hexane.

According to a preferred embodiment of the present invention, said aluminoxane having the general formula (II) may be selected, for example, from: methylaluminoxane (MAO), ethylaluminoxane, n-butylaluminoxane, tetra-isobutylaluminoxane (TIBAO), tert-butylaluminoxane, tetra-(2,4,4-trimethylpentyl)aluminoxane (TIOAO), tetra-(2,3-dimethylbutyl)aluminoxane (TDMBAO), tetra-(2,3,3-trimethylbutyl)aluminoxane (TTMBAO), or mixtures thereof. Methylaluminoxane (MAO) is particularly preferred. Further details relating to the aluminoxane having the general formula (II) may be found, for example, in international patent application WO 2011/061151.

In general, the above-stated catalytic system is preferably formed in an inert liquid medium, more preferably in a hydrocarbon solvent. The pyridyl iron complex having the general formula (I) and the aluminoxane having the general formula (II), as well as the specific methodology used, may be selected on the basis of the molecular structures and the desired result, on the basis of the details similarly reported in the relevant literature available to a person skilled in the art for other transition metal complexes with ligands of various kinds such as, for example, in: Ricci G. et al., "*Advances in Organometallic Chemistry Research*" (2007), Yamamoto K. ed., Nova Science Publisher, Inc., USA, pp. 1-36; Ricci G. et al., "*Coordination Chemistry Reviews*" (2010), vol. 254, pp. 661-676; Ricci G. et al., "*Ferrocenes: Compounds, Properties and Applications*" (2011), Elisabeth S. Phillips ed., Nova Science Publisher, Inc., USA, pp. 273-313; Ricci G. et al., "*Chromium: Environmental, Medical and Material Studies*" (2011), Margaret P. Salden ed., Nova Science Publisher, Inc., USA, pp. 121-1406; Ricci G. et al., "*Cobalt: Characteristics, Compounds, and Applications*" (2011), Lucas J. Vidmar ed., Nova Science Publisher, Inc., USA, pp. 39-81; or Ricci G. et al., "*Phosphorus: Properties, Health effects and Environment*" (2012), Ming Yue Chen and Da-Xia Yang eds., Nova Science Publisher, Inc., USA, pp. 53-94.

For the purpose of the present invention, the aluminoxane having the general formula (II) may be brought into contact with a pyridyl iron complex having the general formula (I), in proportions such that the molar ratio between the aluminium present in the aluminoxane having the general formula (II) and the iron present in the pyridyl iron complex having the general formula (I) is between the above-mentioned values, that is the molar ratio between the aluminium present in the aluminoxane having the general formula (II) and the iron present in the pyridyl iron complex having the general formula (I) is ranging from 5 to 20, preferably ranging from 8 to 12. The sequence in which the pyridyl iron complex having the general formula (I) and the aluminoxane having the general formula (II) are brought into contact with one another is not particularly critical.

For the purpose of the present description and the appended claims, the terms "mole" and "molar ratio" are used both with reference to compounds composed of molecules, and with reference to atoms and ions, so not using the terms gram-atom or atomic ratio for the latter, despite these terms being scientifically more correct.

For the purpose of the present invention, other additives or components may optionally be added to the above-stated catalytic system in such a manner as to adjust it to meet specific practical requirements. The catalytic systems obtained in this manner should thus be considered to be included in the scope of the present invention. Additives and/or components which may be added during preparation and/or formulation of the above-stated catalytic system are, for example: inert solvents, such as, for example, aliphatic and/or aromatic hydrocarbons; aliphatic and/or aromatic ethers; weakly coordinating additives (e.g., Lewis bases) selected, for example, from non-polymerisable olefins; sterically hindered or electron-poor ethers; halogenating agents such as, for example, silicon halides, halogenated, preferably chlorinated, hydrocarbons; or mixtures thereof. Said catalytic system may be prepared, as has already been mentioned above, in accordance with known prior art methods.

For example, said catalytic system may be prepared separately (preformed) and subsequently introduced into the polymerisation environment. In this connection, said catalytic system may be prepared by reacting at least one pyridyl iron complex having the general formula (I) with at least one aluminoxane having the general formula (II), optionally in the presence of other additives or components selected from those mentioned above, in the presence of a solvent such as, for example, toluene, heptane, at temperatures ranging from 20° C. to 60° C., for a time ranging from 10 seconds to 10 hours, preferably ranging from 30 seconds to 5 hours.

Alternatively, said catalytic system may be prepared in situ, i.e. directly in the polymerisation environment. In this connection, said catalytic system may be prepared by separately introducing the pyridyl iron complex having the general formula (I), the aluminoxane having the general formula (II) and the 1,3-butadiene, working under the conditions in which polymerisation is carried out.

Further details relating to the preparation of said catalytic system may be found in the examples shown below.

For the purpose of the present invention, the above-stated catalytic system may also be supported on inert solids, preferably composed of oxides of silicon and/or aluminium, such as, for example, silica, alumina or aluminosilicates. Said catalytic system may be supported using known supporting methods generally involving contact, in a suitable inert liquid medium, between the support, optionally activated by heating to temperatures of above 200° C., and one or both of the components of said catalytic system. It is not necessary, for the purpose of the present invention, for both components to be supported, it also being possible for just the pyridyl iron complex having the general formula (I) or the aluminoxane having the general formula (II) to be present on the surface of the support. In this latter case, the component missing from the surface is subsequently brought into contact with the supported component at the time at which it is desired to form the polymerisation-active catalytic system.

Also included in the scope of the present invention are the pyridyl iron complex having the general formula (I), and the catalytic systems based thereon which have been supported on a solid by means of functionalisation of the latter and formation of a covalent bond between the solid and the pyridyl iron complex having the general formula (I).

The quantity of the pyridyl iron complex having the general formula (I) and of the aluminoxane having the general formula (II) which may be used in the process provided by the present invention varies depending on the polymerisation process it is desired to carry out. As stated above, said quantity is however such as to obtain a molar ratio between the aluminium present in the aluminoxane having the general formula (II) and the iron present in the pyridyl iron complex having the general formula (I) ranging from 5 to 20, preferably ranging from 8 to 12.

According to a preferred embodiment of the present invention, said process may be carried out in the presence of at least one inert organic solvent selected, for example, from: saturated aliphatic hydrocarbons such as, for example, butane, pentane, hexane, heptane, or mixtures thereof; saturated cycloaliphatic hydrocarbons such as, for example, cyclopentane, cyclohexane, or mixtures thereof; mono-olefins such as, for example, 1-butene, 2-butene, or mixtures thereof; aromatic hydrocarbons such as, for example, benzene, toluene, xylene, or mixtures thereof; halogenated hydrocarbons such as, for example, methylene chloride, chloroform, carbon tetrachloride, trichloroethylene, perchloroethylene, 1,2-dichloroethane, chlorobenzene, bromobenzene, chlorotoluene, or mixtures thereof. Hexane, heptane, toluene are preferred.

According to a preferred embodiment of the present invention, in said process the concentration of 1,3-butadiene in said inert organic solvent may be ranging from 5% by weight to 50% by weight, preferably ranging from 10% by weight to 20% by weight, based on the total weight of the 1,3-butadiene/inert organic solvent mixture.

According to a preferred embodiment of the present invention, said process may be carried out at temperatures ranging from −30° C. to +60° C., preferably ranging from −20° C. to +30° C.

With regard to pressure, it is preferable to work at the pressure of the components of the mixture which is to be polymerised.

Said process may be carried out either continuously or "batchwise", preferably continuously.

The process object of the present invention makes it possible to obtain a syndiotactic 1,2-polybutadiene having the following characteristics:

1,2 unit content of greater than or equal to 60%, preferably ranging from 70% to 90%;

syndiotactic triad content (rr %) of greater than or equal to 50%, preferably ranging from 60% to 75%;

melting point of greater than or equal to 65° C., preferably ranging from 67° C. to 120° C.;

crystallisation temperature of greater than or equal to 40° C., preferably ranging from 45° C. to 85° C.;

weight-average molecular weight ($M_w$) ranging from 300000 g×mol$^{-1}$ to 400000 g×mol$^{-1}$, preferably ranging from 310000 g×mol$^{-1}$ to 360000 g×mol$^{-1}$.

The syndiotactic 1,2-polybutadiene obtained by the process object of the present invention may advantageously be used in various sectors such as, for example, in the footwear industry, in particular in the production of shoe soles.

The present invention accordingly further provides use of the syndiotactic 1,2-polybutadiene obtained by the above-described process in the footwear industry, in particular in the production of shoe soles.

Figure 1:
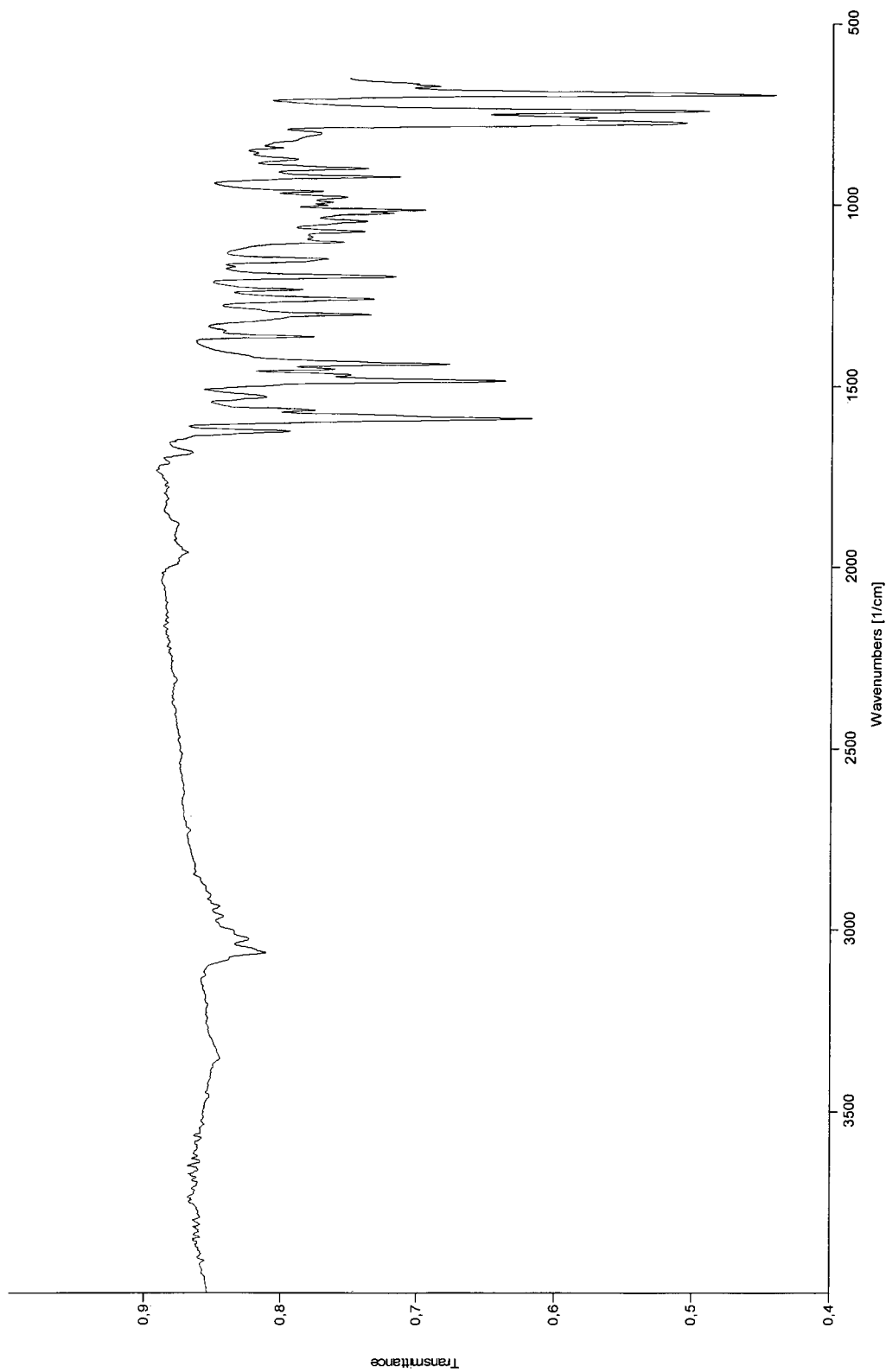
FIG. 1 shows the FR-IR spectrum (solid state, UATR) of the FeCl$_2$(L1) complex obtained in Example 4.

Some illustrative, non-limiting examples of the present invention are provided below to assist in understanding the present invention and the implementation thereof.

EXAMPLES

Reactants and Materials

The following list shows the reactants and materials used in the subsequent examples of the invention, any optional pretreatments and the manufacturers thereof:

iron powder (Fe) (Aldrich): purity 99%, used as such;
iron trichloride ($FeCl_3$) (Aldrich): purity 99.9%, used as such;
iron dichloride ($FeCl_2$) (Aldrich): purity 97%, used as such;
iron dichloride:tetrahydrofuran complex (1:1.9) [$FeCl_2$(THF)$_{1.9}$]: prepared from iron powder (Fe) and iron trichloride ($FeCl_3$), in tetrahydrofuran (THF) with heat, according to the method reported by Cotton F. A. et al., in "*Inorganic Chimica Acta*" (1991), vol. 179, pp. 11-15;
methylaluminoxane (MAO) (10% by weight solution in toluene) (Crompton): used as such;
aniline (Aldrich): distilled under reduced pressure and stored under an inert atmosphere;
hydrochloric acid, 37% aqueous solution (Aldrich): used as such;
o-toluidine (Aldrich): distilled under reduced pressure and stored under an inert atmosphere;
2-iso-propylaniline (Aldrich): used as such;
2-pyridinecarboxaldehyde (Aldrich): used as such;
2-acetylpyridine (Aldrich): used as such;
ethyl acetate (Aldrich): used as such;
p-toluenesulfonic acid monohydrate (Aldrich): 98.5%, used as such;
heptane (Aldrich): pure, ≥99%, distilled over sodium (Na) under an inert atmosphere;
pentane (Aldrich): pure, ≥99%, distilled over sodium (Na) under an inert atmosphere;
methanol (Carlo Erba, RPE): used as such;
toluene (Aldrich): pure, ≥99.5%, distilled over sodium (Na) under an inert atmosphere;
cobalt dichloride ($CoCl_2$) (Strem Chemicals): used as such;
di-triphenylphosphine (Strem Chemicals): used as such;
ethanol (Carlo Erba, RPE): used as such;
1,3-butadiene (Air Liquide): pure, ≥99.5%, evaporated from the container before each production, dried by being passed through a column packed with molecular sieves and condensed inside the reactor which has been pre-cooled to −20° C.;
formic acid (HCOOH) (Aldrich): purity ≥95%, used as such;
hydrochloric acid (HF) (40% aqueous solution) (Aldrich): used as such;
sulfuric acid ($H_2SO_4$) (96% aqueous solution) (Aldrich): used as such, or diluted with distilled water (1:5);
nitric acid ($HNO_3$) (70% aqueous solution) (Aldrich): used as such;
sodium carbonate ($Na_2CO_3$) (Aldrich): used as such;
silver nitrate ($AgNO_3$) (Aldrich): used as such;
deuterated tetrachloroethylene ($C_2D2Cl_4$) (Acros): used as such;
hexamethyldisiloxane (HMDS) (Acros): used as such;
deuterated chloroform ($CDCl_3$) (Acros): used as such;
tetramethylsilane (TMS) (Acros): used as such.

The analysis and characterisation methods stated below were used.

Elemental Analysis a) Determination of Fe

The quantity by weight of iron (Fe) in the pyridyl iron complexes used for the purpose of the present invention was determined by placing an accurately weighed aliquot, working in a dry box under a stream of nitrogen, of approx. 30 mg-50 mg of sample in an approx. 30 ml platinum crucible, together with a mixture of 1 ml of 40% hydrofluoric acid (HF), 0.25 ml of 96% sulfuric acid ($H_2SO_4$) and 1 ml of 70% nitric acid ($HNO_3$). The crucible was then heated on a plate, increasing the temperature until white sulfuric fumes appeared (approx. 200° C.). The mixture obtained was cooled to room temperature, 1 ml of 70% nitric acid ($HNO_3$) was added and then heated again until fumes appeared. Once the sequence had been repeated twice, a clear, almost colourless solution was obtained. 1 ml of nitric acid ($HNO_3$) and approx. 15 ml of water were then added cold and the temperature was raised to 80° C. for approx. 30 minutes. The sample so prepared was diluted with MilliQ purity water to an accurately weighed weight of approx. 50 g, in order to obtain a solution on which an instrumental analytical determination was performed by means of a Thermo Optek IRIS Advantage Duo ICP-OES spectrometer (plasma with optical detection) by comparison with solutions of known concentration. For this purpose, a calibration curve in the range from 0 ppm-10 ppm was prepared for each analyte by measuring solutions of known titre obtained by weight dilution of certified solutions.

The solution of the sample prepared as above was again weight-diluted in such a manner as to obtain concentrations close to the reference concentrations prior to carrying out spectrophotometric detection. All samples were prepared in duplicate. The results were considered acceptable if the individual results of the duplicate tests differed by no more than 2% relative with respect to the mean value thereof.

b) Determination of Chlorine

To this end, approx. 30 mg-50 mg samples of the pyridyl iron complexes used for the purpose of the present invention were accurately weighed into 100 ml glass beakers in a dry box under a stream of nitrogen. 2 g of sodium carbonate ($Na_2CO_3$) were added and, outside the dry box, 50 ml of MilliQ water. The mixture was brought to the boil on a plate and stirred with a magnetic stirrer for approx. 30 minutes. The mixture was left to cool, sulfuric acid ($H_2SO_4$) diluted to 1:5 was added until an acidic reaction was obtained and titration was performed with 0.1 N silver nitrate ($AgNO_3$) with a potentiometric titrator.

c) Determination of Carbon, Hydrogen, Nitrogen and Phosphorus

Carbon, hydrogen and nitrogen were determined in the pyridyl iron complexes used for the purpose of the present invention, and in the ligands used for the purpose of the present invention, using a Carlo Erba model 1106 automatic analyser.

$^{13}$C-HMR and $^1$H-HMR Spectra

The $^{13}$C-HMR and $^1$H-HMR spectra were recorded with a Bruker Avance 400 nuclear magnetic resonance spectrometer using deuterated tetrachloroethylene ($C_2D2Cl_4$) at 103° C. and hexamethyldisiloxane (HDMS) as internal standard, or using deuterated chloroform ($CDCl_3$) at 25° C. and tetramethylsilane (TMS) as internal standard. Polymer solutions having concentrations of 10% by weight based on the total weight of the polymer solution were used for this purpose.

The microstructure of the polymers [i.e. content of 1,4-cis (%) and 1,2(%) units and content of syndiotactic triads (rr %)] was determined by analysing the above-stated spectra on the basis the description in the literature by Mochel, V. D., in "*Journal of Polymer Science Part A-1: Polymer Chemistry*" (1972), vol. 10, issue 4, pp. 1009-1018.

FT-IR Spectra (Solid State, UATR)

The FT-IR spectra (solid state, UATR) were recorded by means of a Bruker IFS 48 spectrophotometer equipped with a Thermo Spectra-Tech horizontal ATR attachment. The section in which the samples are placed for analysis is a Fresnel ATR accessory (Shelton, Conn., USA) which uses zirconium selenide crystals (ZnSe) with an angle of incidence of 45° in the horizontal direction.

The FT-IR spectra (solid state, UATR) of the pyridyl iron complexes used for the purpose of the present invention were obtained by inserting samples of the pyridyl iron complex for analysis into said section.

IR Spectra

The IR (FTIR) spectra were recorded by means of Thermo Nicolet Nexus 670 and Bruker IFS 48 spectrophotometers.

The IR (FTIR) spectra of the polymers were obtained from polymer films on potassium bromide (KBr) pellets, said films being obtained by deposition of a solution of the polymer for analysis in hot 1,2-dichlorobenzene. The concentration of the analysed polymer solutions was 10% by weight based on the total weight of the polymer solution.

Determination of Molecular Weight

The molecular weight (MW) of the polymers obtained was determined by GPC ("Gel Permeation Chromatography") using a Waters® Alliance® GPCN 2000 System from Waters Corporation which uses two detection lines: refractive index (RI) and viscometer working under the following conditions:

two PLgel Mixed-B columns;
solvent/eluent: o-dichlorobenzene (Aldrich);
flow rate: 0.8 ml/min;
temperature: 145° C.;
calculation of molecular mass: Universal Calibration method.

The weight-average molecular weight ($M_w$) and polydispersity index (PDI) corresponding to the ratio $M_w/M_n$ ($M_n$=number-average molecular weight) are reported.

X-Ray Diffractometry (XRD) X-Ray Spectrum

To this end, samples of the polymers obtained in powder form (approx. 100 mg), were analysed by X-ray diffractometry (XRD) using a Bruker P4 diffractometer equipped with a HiStar 2D detector using graphite-monochromatised Cu KR radiation ($\lambda$) (1.54179 Å) and a sample-detector distance of 10 cm.

Thermal Analysis (DSC)

DSC ("Differential Scanning Calorimetry") thermal analysis for the purpose of determining the melting point ($T_m$) and crystallisation temperature ($T_c$) of the polymers obtained was carried out using a Perkin Elmer Pyris differential scanning calorimeter. To this end, 5 mg of polymer were analysed at a scanning speed ranging from 1° C./min to 20° C./min under an inert nitrogen atmosphere.

Example 1

Synthesis of the Ligand Having the Formula (L1)

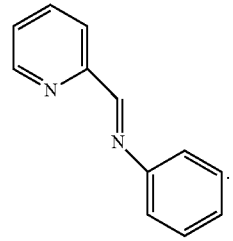

(L1)

2-Pyridinecarboxaldehyde (30 g; 280 mmol) and a few drops of formic acid were added to a solution of aniline (26.1 g; 280 mmol) in methanol (250 ml), in a 500 ml reaction flask: the mixture obtained was left to stand, under stirring, at room temperature, for 48 hours. The solvent was then removed by vacuum evaporation and the residue obtained was purified by elution on a silica gel chromatographic column [eluent: 99/1 (vol/vol) heptane/ethyl acetate mixture], 38 g of a pale yellow solid (yield=74.5%) corresponding to the ligand having the formula (L1), being obtained.

Molecular weight (MW): 182.22.

Elemental analysis [found (calculated for $C_{12}H_{10}N_2$)]: C: 80.00% (79.10%); H: 5.83% (5.53%); N: 15.71% (15.37%).

$^1$H-NMR (CDCl$_3$, δ ppm) 8.70 (m, 1H, HPy), 8.41 (m, 1H, HPy), 8.80 (tds, 1H CH=N), 8.19 (d, 1H, HPy), 7.77 (dt, 1H, HPy), 7.23-7.42 (m, 1H, HPy; m, 5H, Ar).

Example 2

Synthesis of the Ligand Having the Formula (L2)

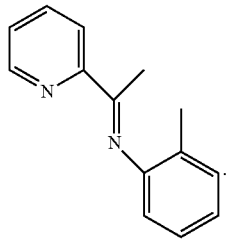

(L2)

2-Acetylpyridine (9.1 g; 75 mmol) and a few drops of formic acid were added to a solution of o-toluidine (8 g; 75 mmol) in methanol (100 ml), in a 250 ml reaction flask: the mixture obtained was left to stand, under stirring, at room temperature, for 48 hours. The solvent was then removed by vacuum evaporation and the residue obtained was purified by elution on a silica gel chromatographic column [eluent: 99/1 (vol/vol) heptane/ethyl acetate mixture], 6.5 g of a yellowish oil (yield=40%) corresponding to the ligand having the formula (L2), being obtained.

Molecular weight (MW): 210.28.

Elemental analysis [found (calculated for $C_{14}H_{14}N_2$)]: C: 80.00% (79.97%); H: 6.77% (6.71%); N: 13.41% (13.32%).

$^1$H-NMR (CDCl$_3$, δ ppm): 8.70 (m, 1H, HPy), 8.41 (m, 1H, HPy), 8.80 (td, 1H, HPy), 7.39 (dt, 1H, HPy), 7.27-7.18 (m, 2H, Ph), 7.02 (m, 1H, Ph), 6.69 (d, 1H, Ph), 2.30 (s, 3H, N=C—CH$_3$), 2.10 (s, 3H, Ph-CH$_3$).

Example 3

Synthesis of the Ligand Having the Formula (L3)

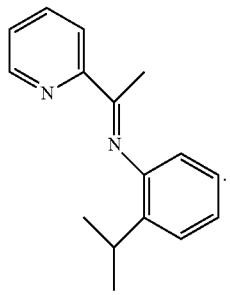

(L3)

2-Acetylpyridine (3.78 g; 31.1 mmol) and p-toluenesulfonic acid monohydrate (0.15 g; 0.81 mmol) were added to a solution of 2-iso-propylaniline (4.20 g; 31.1 mmol) in toluene (20 ml), in a 500 ml reaction flask: the mixture obtained was refluxed for 2 hours. The solvent was then removed by vacuum evaporation and the residue obtained was purified by distillation under vacuum, 5.89 g of an orange oil (yield=79%), corresponding to the ligand having the formula (L3), being obtained.

FT-IR (Nujol): (cm$^{-1}$): 1637 ($v_{C=N}$).

Molecular weight (MW): 238.

Elemental analysis [found (calculated for $C_{16}H_{18}N_2$)]: C: 80.17% (80.63%); H: 7.80% (7.61%); N: 11.91% (11.75%).

FT-IR (solid state, UATR) (cm$^{-1}$): 1637 ($v_{C=N}$).

$^1$H-NMR (CDCl$_3$, δ ppm) 8.71 (d, 1H), 8.37 (d, 1H), 7.81 (t, 1H), 7.38 (m, 2H), 7.22 (t, 1H), 7.15 (t, 1H), 6.67 (d, 1H), 3.05 (sept, 1H), 2.39 (s, 3H), 1.23 (d, 6H).

Example 4

Synthesis of FeCl$_2$(L1) [Sample MG82A]

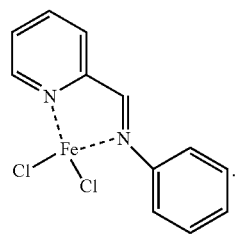

(MG82A)

The iron dichloride:tetrahydrofuran (1:1.9) complex [FeCl$_2$(THF)$_{1.9}$] (171 mg; 0.65 mmol) was added to a solution of the ligand having the formula (L1) (118 mg; 0.65 mmol; molar ratio L1/Fe=1), obtained as described in Example 1, in toluene (20 ml) in a 100 ml reaction flask: the mixture obtained was left to stand, under stirring, at 100° C., for 3 hours. The supernatant was then removed by evaporation under reduced pressure and the residue obtained was washed with heptane (2×15 ml) and dried under vacuum, at room temperature, 156 mg of a blue solid product corresponding to the FeCl$_2$(L1) complex being obtained, this amounting to conversion of 78% based on the introduced iron dichloride:tetrahydrofuran (1:1.9) complex [FeCl$_2$(THF)$_{1.9}$].

Molecular weight (MW): 308.97.

Elemental analysis [found (calculated for $C_{12}H_{10}Cl_2FeN_2$)]: C: 46.01% (46.65%), H: 3.02% (3.26%), N: 9.58% (9.07%), Cl: 22.03% (22.95%), Fe: 16.05% (16.89%).

FIG. 1 shows the FT-IR spectrum (solid state, UATR) of the FeCl$_2$(L1) complex obtained.

Example 5

Synthesis of FeCl$_2$(L2) [sample MG215]

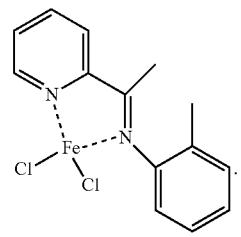

(MG215)

Iron dichloride (FeCl$_2$) (319 mg; 2.51 mmol) was added to a solution of the ligand having the formula (L2) (527 mg; 2.51 mmol; molar ratio L2/Fe=1), obtained as described in Example 2, in toluene (20 ml), in a 100 ml reaction flask: the mixture obtained was left to stand, under stirring, at 100° C., for 3 hours. The supernatant was then removed by evaporation under reduced pressure and the residue obtained was washed with heptane (2×15 ml) and dried under vacuum, at room temperature, 521 mg of a pale blue solid product corresponding to the FeCl$_2$(L2) complex being obtained, this amounting to conversion of 62% based on the introduced iron dichloride (FeCl$_2$).

Molecular weight (MW): 337.03

Elemental analysis [found (calculated for C$_{14}$H$_{14}$Cl$_2$FeN$_2$)]: C: 49.10% (49.89%), H: 4.38% (4.19%), N: 8.21% (8.31%), Cl: 21.42% (21.04%), Fe: 16.82% (16.57%).

FT-IR (Nujol) (cm$^{-1}$): 1628 ($\nu_{C=N}$).

Figure 2:
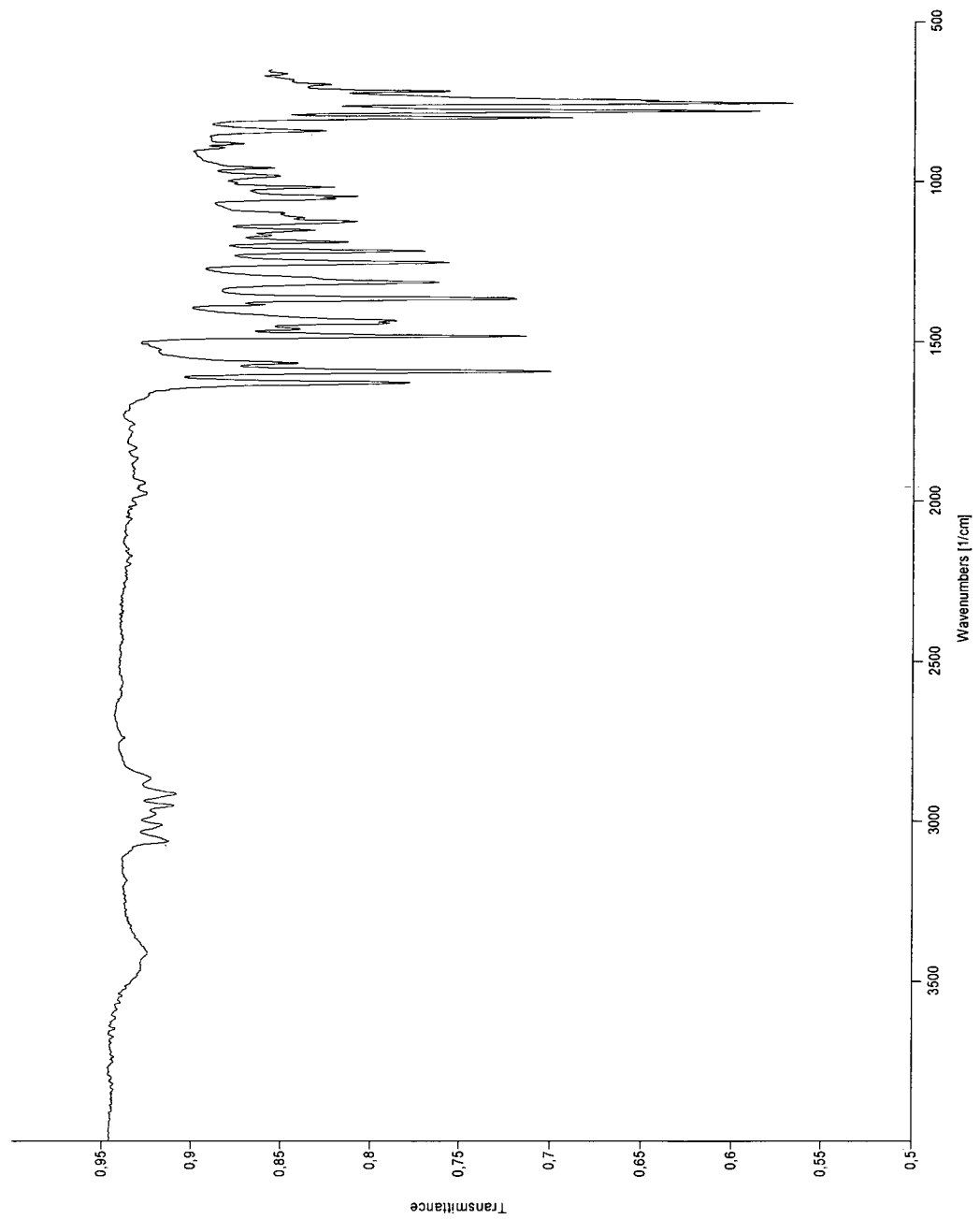
FIG. 2 shows the FT-IR spectrum (solid state, UATR) of the FeCl$_2$(L2) complex obtained in Eample 5.

FIG. 2 shows the FT-IR spectrum (solid state, UATR) of the FeCl$_2$(L2) complex obtained.

Example 6

Synthesis of FeCl$_2$(L3) [Sample MG212]

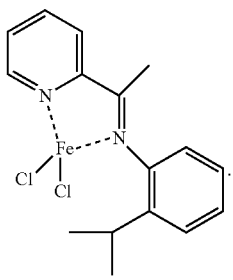

(MG212)

Iron trichloride (FeCl$_2$) (288 mg; 2.27 mmol) was added to a solution of the ligand having the formula (L3) (540 mg; 2.27 mmol; molar ratio L3/Fe=1), obtained as described in Example 3, in toluene (20 ml), in a 100 ml reaction flask: the mixture obtained was left to stand, under stirring, at 100° C., for 3 hours. The supernatant was then removed by evaporation under reduced pressure and the residue obtained was washed with heptane (2×15 ml) and dried under vacuum, at room temperature, 665 mg of a pale blue solid product corresponding to the FeCl$_2$(L3) complex being obtained, this amounting to conversion of 80% based on the introduced iron trichloride (FeCl$_2$).

Molecular weight (MW): 3665.08.

Elemental analysis [found (calculated for C$_{16}$H$_{18}$Cl$_2$FeN$_2$)]: C: 52.12% (52.64%), H: 4.65% (4.96%), N: 7.26% (7.67%), Cl: 19.02% (19.42%), Fe: 15.04% (15.30%).

Figure 3:
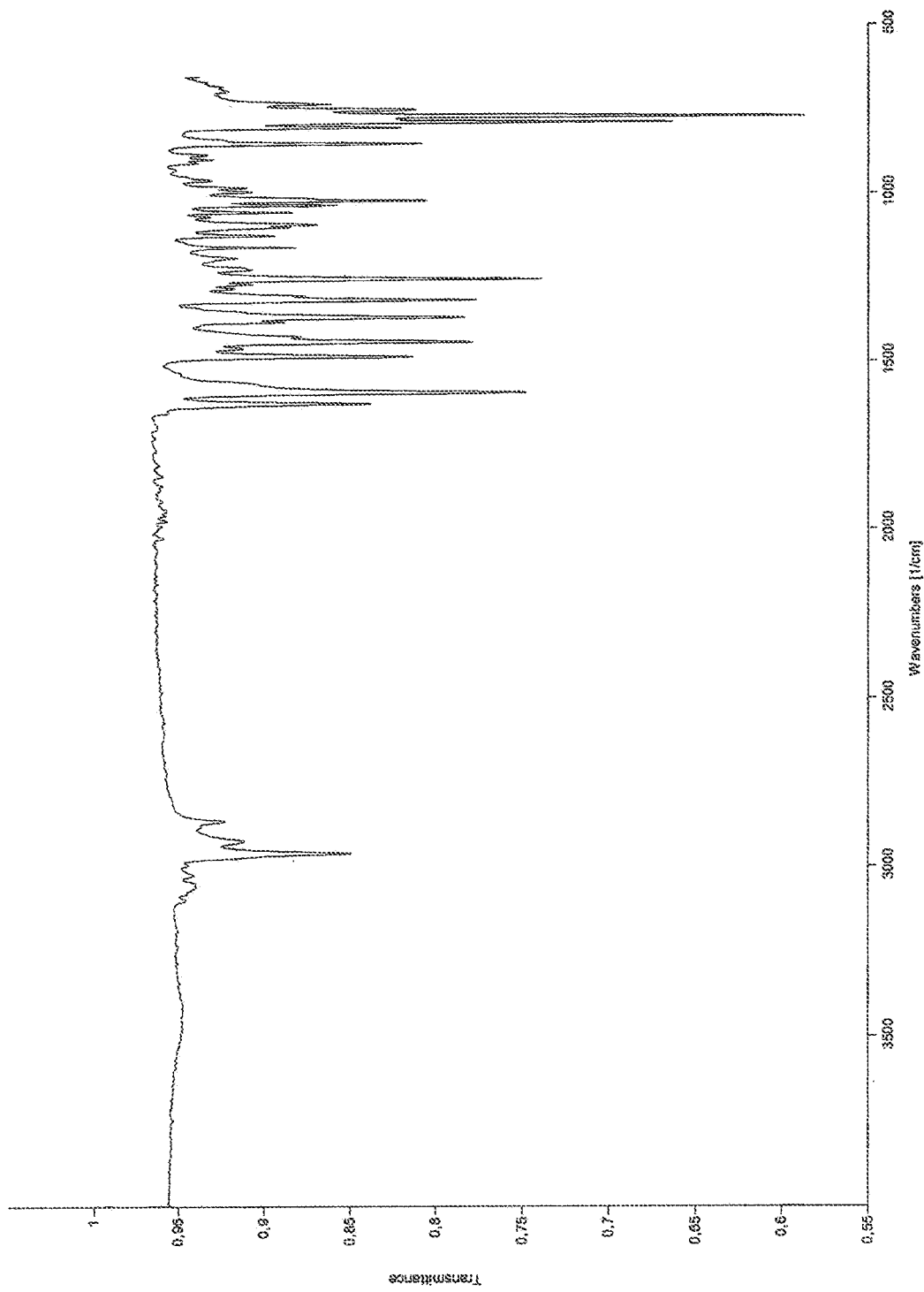
FIG. 3 shows the FT-IR spectrum (solide state, UATR) of the FeCl$_3$(L1) complex obtained in Example 6.

FIG. 3 shows the FT-IR spectrum (solid state, UATR) of the FeCl$_3$(L1) complex obtained.

Example 7

Synthesis of FeCl$_3$(L1) [Sample MG87]

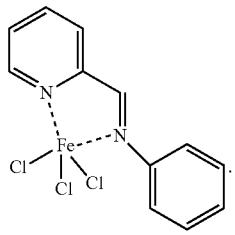

(MG87)

Iron trichloride (FeCl$_3$) (225 mg; 1.39 mmol) was added to a solution of the ligand having the formula (L1) (253 mg; 1.39 mmol; molar ratio L1/Fe=1), obtained as described in Example 1, in toluene (20 ml), in a 100 ml reaction flask: the mixture obtained was left to stand, under stirring, at room temperature, for 3 hours. The supernatant was then removed by evaporation under reduced pressure and the residue obtained was washed with heptane (2×15 ml) and dried under vacuum, at room temperature, 203 mg of a brown solid product corresponding to the FeCl$_3$(L1) complex being obtained, this amounting to conversion of 42% based on the introduced iron trichloride (FeCl$_3$).

Molecular weight (MW): 344.43.

Elemental analysis [found (calculated for C$_{12}$H$_{10}$Cl$_3$FeN$_2$)]: C: 41.20% (41.84%), H: 2.35% (2.92%), N: 7.88% (8.13%), Cl: 31.25% (30.88%), Fe: 15.84% (16.21%).

Figure 4:
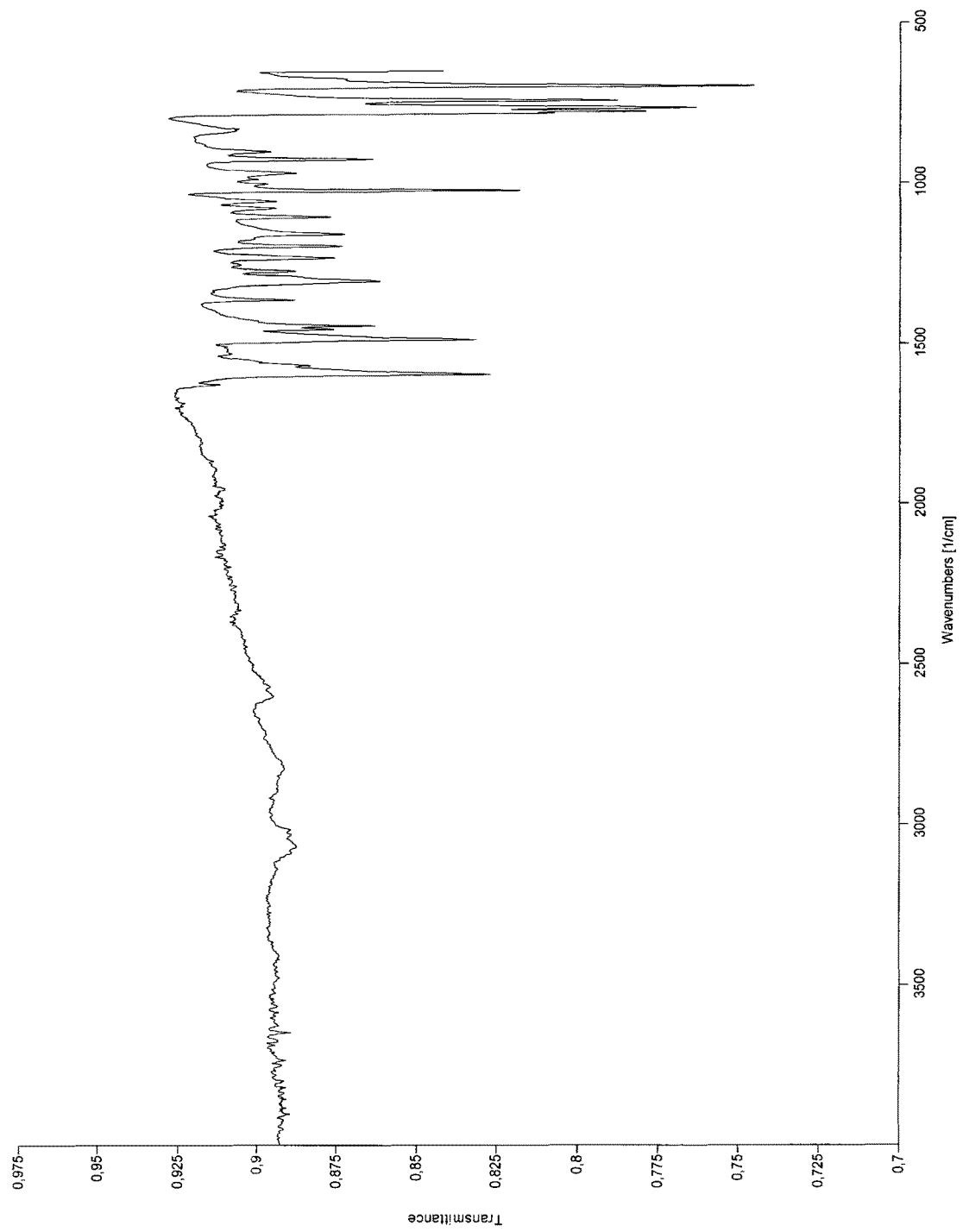
FIG. 4 shows the FT-IR spectrum (solide state, UATR) of the FeCl$_3$(L1) complex obtained in Example 7.

FIG. 4 shows the FT-IR spectrum (solid state, UATR) of the FeCl$_3$(L1) complex obtained.

Example 8

Synthesis of FeCl$_3$(L2) [Sample MG213]

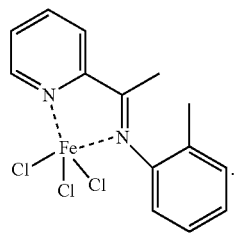

(MG213)

Iron trichloride (FeCl$_3$) (225 mg; 1.39 mmol) was added to a solution of the ligand having the formula (L2) (293 mg; 1.39 mmol; molar ratio L2/Fe=1), obtained as described in Example 2, in toluene (20 ml), in a 100 ml reaction flask: the mixture obtained was left to stand, under stirring, at room temperature, for 3 hours. The supernatant was then removed by evaporation under reduced pressure and the residue obtained was washed with heptane (2×15 ml) and dried under vacuum, at room temperature, 396 mg of a brown solid product corresponding to the FeCl$_3$(L2) complex being obtained, this amounting to conversion of 76% based on the introduced iron trichloride (FeCl$_3$).

Molecular weight (MW): 372.48.

Elemental analysis [found (calculated for C$_{14}$H$_{14}$Cl$_3$FeN$_2$)]: C: 45.00% (45.14%), H: 3.69% (3.79%), N: 7.69% (7.52%), Cl: 28.96% (28.55%), Fe: 15.09% (14.99%).

Figure 5:
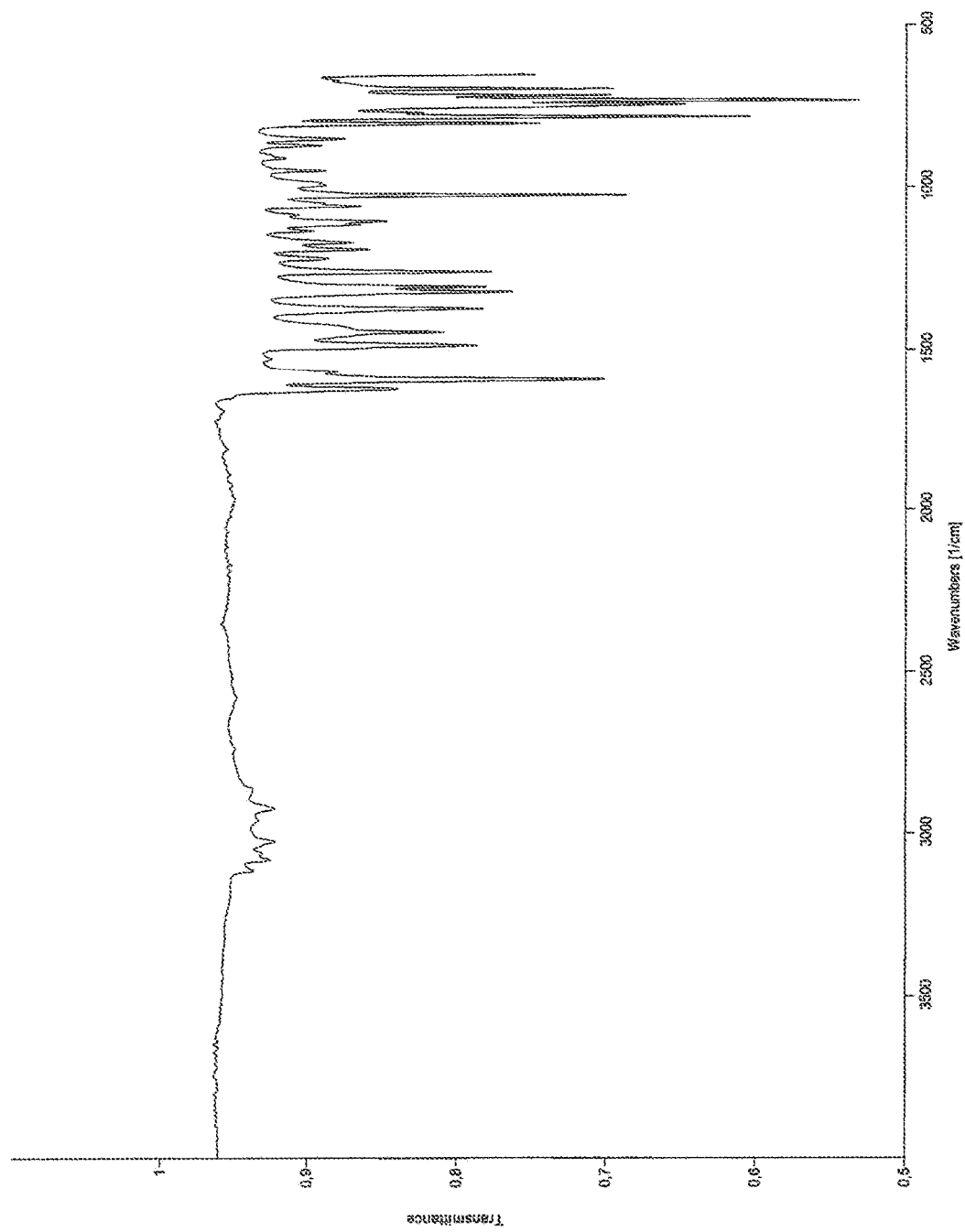
FIG. 5 shows the FT-IR spectrum (solide state, UATR) of the FeCl$_3$(L2) complex obtained in Example 8.

FIG. 5 shows the FT-IR spectrum (solid state, UATR) of the FeCl$_3$(L2) complex obtained.

Example 9

Synthesis of FeCl$_3$(L3) [Sample MG208]

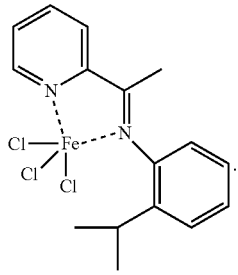

(MG208)

Iron trichloride (FeCl$_3$) (350 mg; 2.16 mmol) was added to a solution of the ligand having the formula (L3) (514 mg; 2.16 mmol; molar ratio L3/Fe=1), obtained as described in Example 3, in toluene (20 ml), in a 100 ml reaction flask: the mixture obtained was left to stand, under stirring, at room temperature, for 3 hours. The supernatant was then removed by evaporation under reduced pressure and the residue obtained was washed with heptane (2×15 ml) and dried under vacuum, at room temperature, 821 mg of a red solid product corresponding to the FeCl$_3$(L3) complex being obtained, this amounting to conversion of 95% based on the introduced iron trichloride (FeCl$_3$).

Molecular weight (MW): 400.35.

Elemental analysis [found (calculated for C$_{16}$H$_{18}$Cl$_3$FeN$_2$)]: C: 48.09% (47.97%), H: 4.71% (4.53%), N: 6.65% (6.99%), Cl: 25.96% (26.55%), Fe: 14.08% (13.94%).

Figure 6:
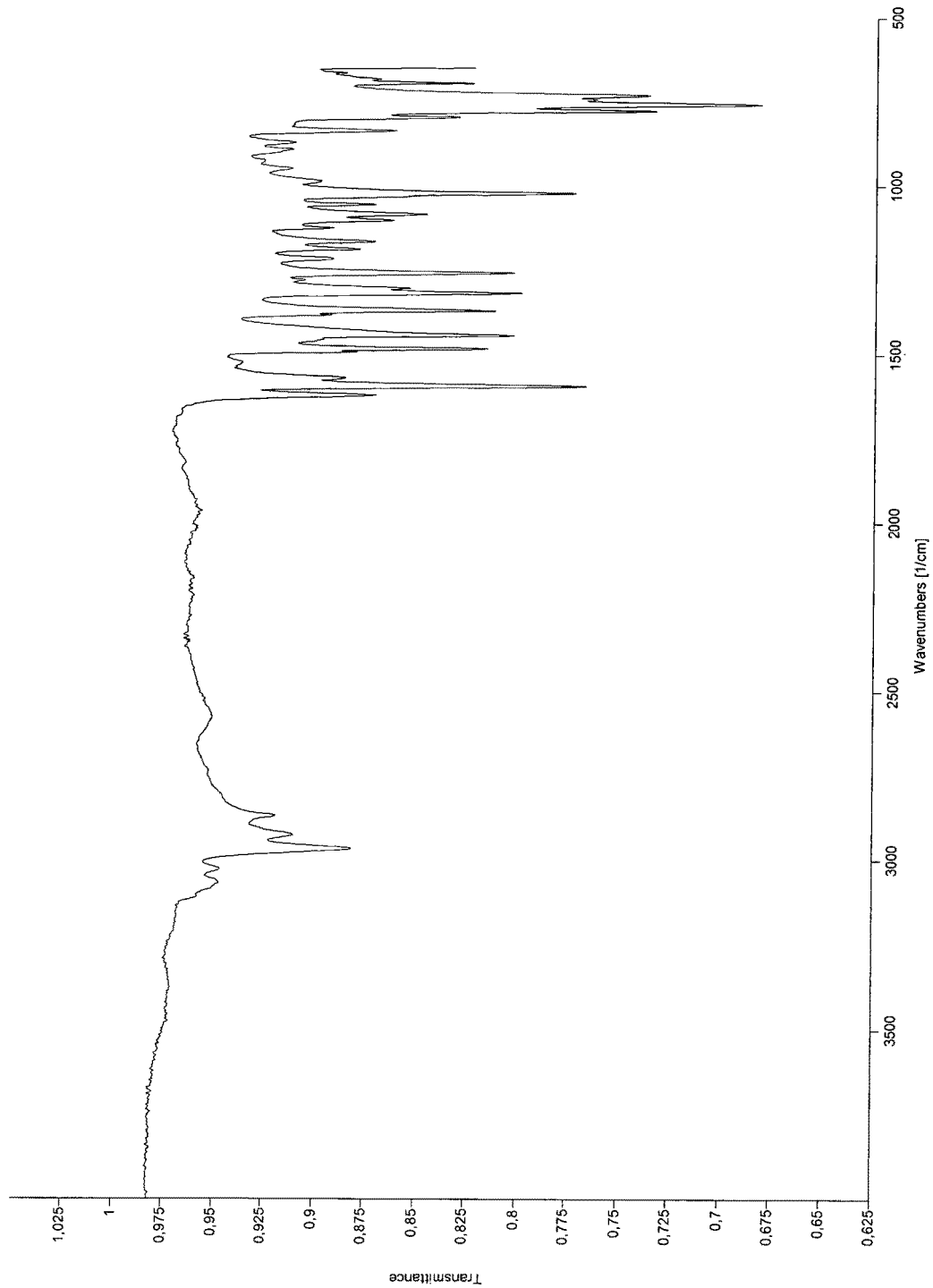
FIG. 6 shows the FT-IR spectrum (solide state, UATR) of the FeCl$_3$(L3) complex obtained in Example 9.

FIG. 6 shows the FT-IR spectrum (solid state, UATR) of the FeCl$_3$(L3) complex obtained.

Example 10 (G1525)

2 ml of 1,3-butadiene, equal to approx. 1.4 g, were condensed at low temperature (−20° C.) in a 25 ml tube. 14.4 ml of toluene were then added and the temperature of the solution obtained in this manner was adjusted to +20° C. Methylaluminoxane (MAO) in a solution in toluene (0.063 ml; 1×10$^{-4}$ moles, equal to approx. 5.8 g) was then added, followed by the complex FeCl$_2$(L1) [sample MG82A] (1.54 ml of suspension in toluene at a concentration of 2 mg/ml; 1×10$^{-5}$ moles, equal to approx. 3.08 mg) obtained as described in Example 3. The whole was left to stand, under magnetic stirring, at +20° C., for 45 minutes.

Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 7:
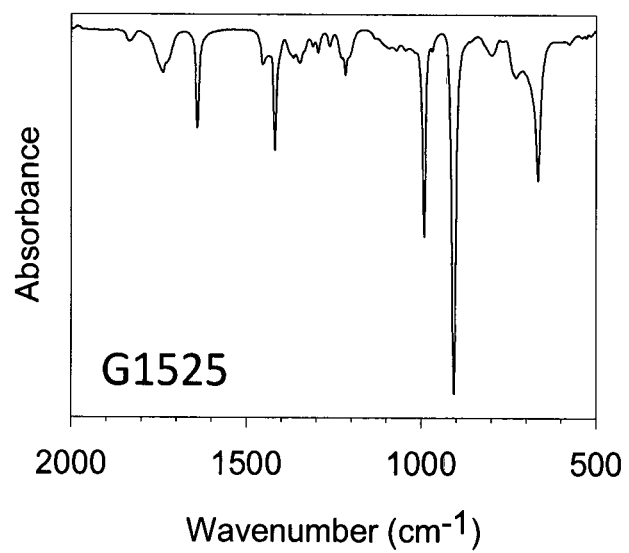
FIG. 7 shows the FT-IR spectrum of the syndiotactic 1,2-polybutadiene obtained in Example 10.

FIG. 7 shows the FT-IR spectrum of the syndiotactic 1,2-polybutadiene obtained.

Figure 8:
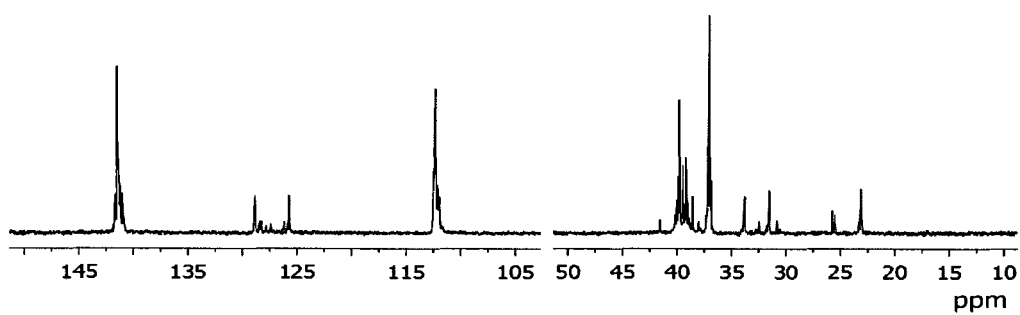
FIG. 8 shows the $^1$H-NMR (top) and $^{13}$C-NMR (bottom) spectra of the syndiotactic 1,2-polybutadiene obtained in Example 10.
Figure 8:
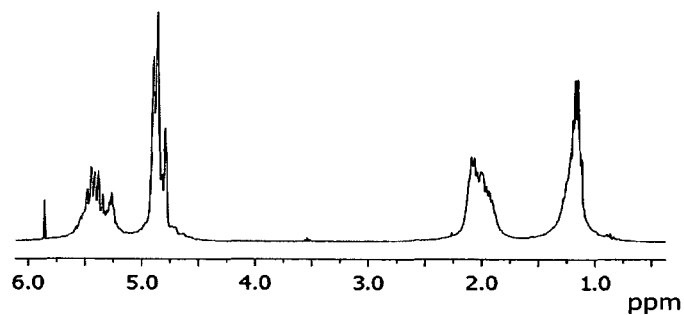

FIG. 8 shows the $^1$H-NMR (top) and $^{13}$C-NMR (bottom) spectra of the syndiotactic 1,2-polybutadiene obtained.

Figure 9:
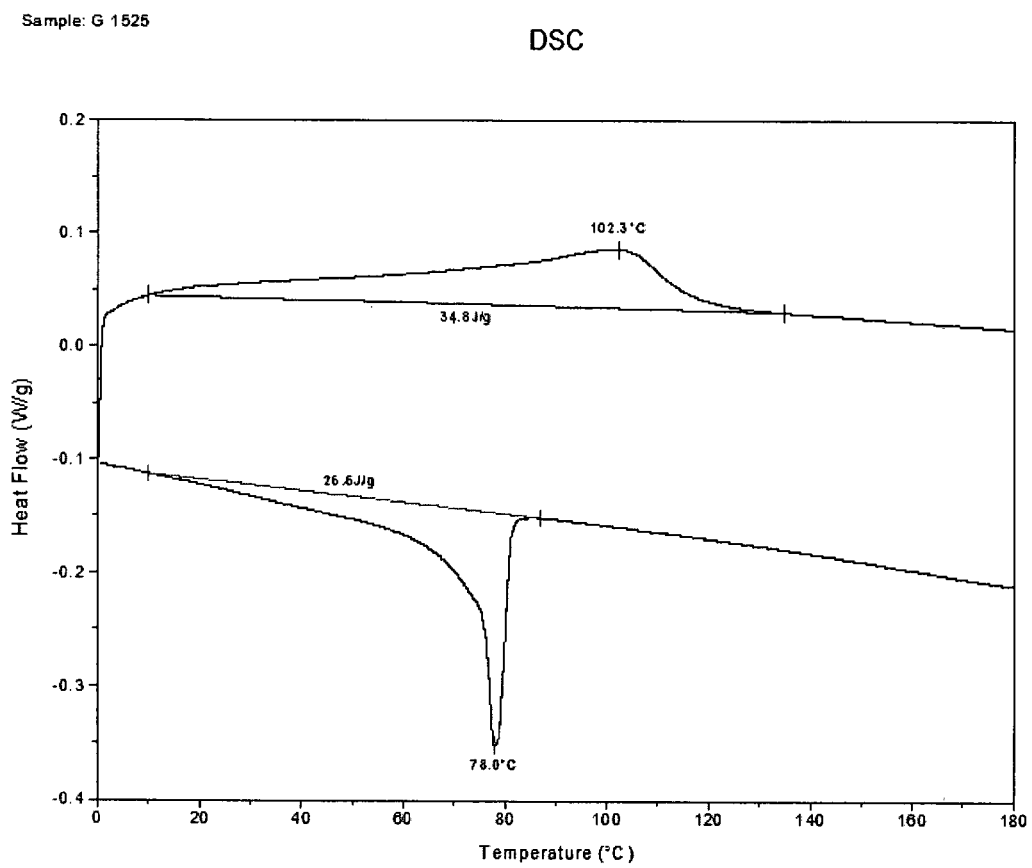
FIG. 9 shows the DSC curve of the syndiotactic 1,2-polybutadiene obtianed Example 10.

FIG. 9 shows the DSC curve of the syndiotactic 1,2-polybutadiene obtained.

Figure 10:
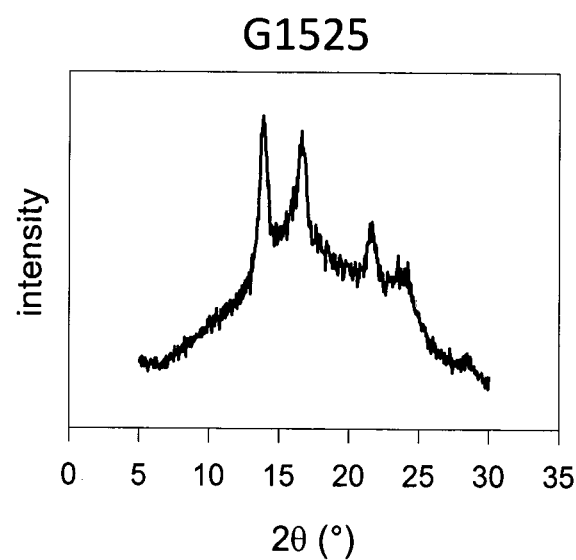
FIG. 10 shows the X-ray spectrum of the syndiotactic 1,2-polybutadiene obtained in Example 10.

FIG. 10 shows the X-ray spectrum of the syndiotactic 1,2-polybutadiene obtained.

Example 11 (G1524)

2 ml of 1,3-butadiene, equal to approx. 1.4 g, were condensed at low temperature (−20° C.) in a 25 ml tube. 14.25 ml of toluene were then added and the temperature of the solution obtained in this manner was adjusted to +20° C. Methylaluminoxane (MAO) in a solution in toluene (0.063 ml; 1×10$^{-4}$ moles, equal to approx. 5.8 g) was then added, followed by the complex FeCl$_2$(L2) [sample MG215] (1.69 ml of suspension in toluene at a concentration of 2 mg/ml; 1×10$^{-5}$ moles, equal to approx. 3.38 mg) obtained as described in Example 4. The whole was left to stand, under magnetic stirring, at +20° C., for 45 minutes.

Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 11:
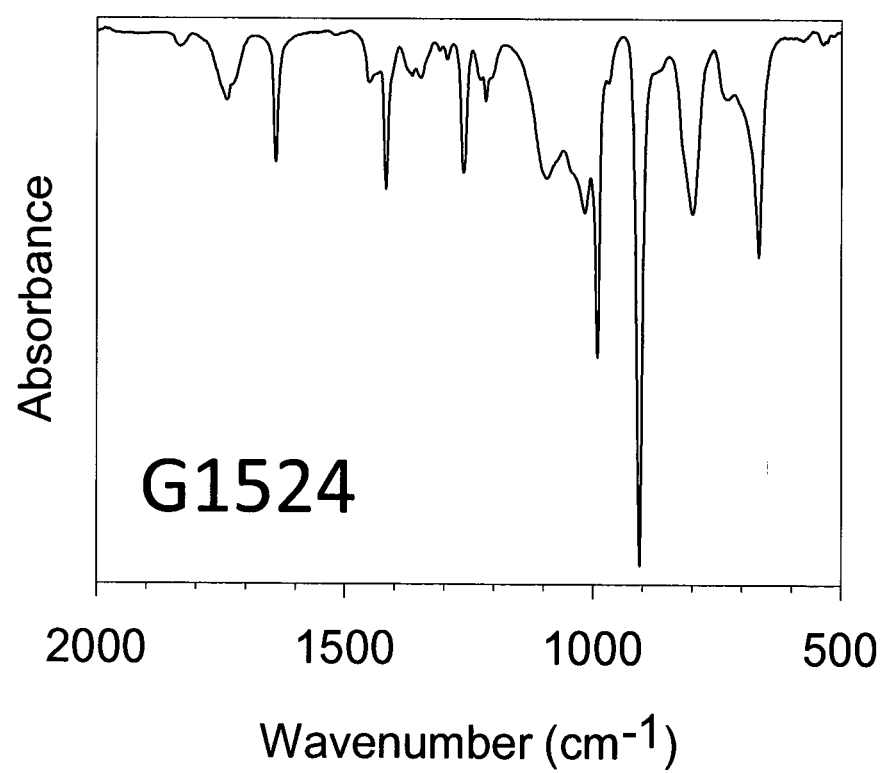
FIG. 11 shows the FT-IR spectrum of the syndiotactic 1,2-polybutadiene obtained in Example 11.

FIG. 11 shows the FT-IR spectrum of the syndiotactic 1,2-polybutadiene obtained.

Figure 12:
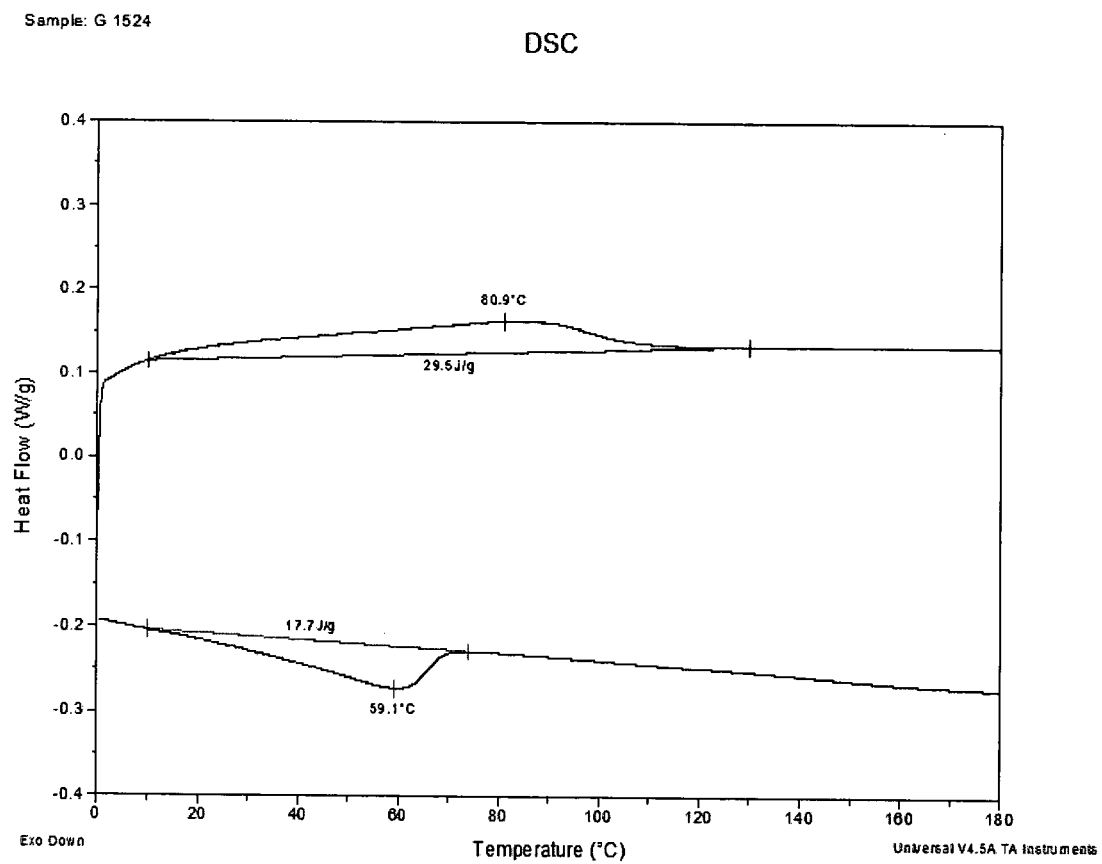
FIG. 12 shows the DSC curve of the syndiotactic 1,2-polybutadiene obtained in Example 11.

FIG. 12 shows the DSC curve of the syndiotactic 1,2-polybutadiene obtained.

Figure 13:
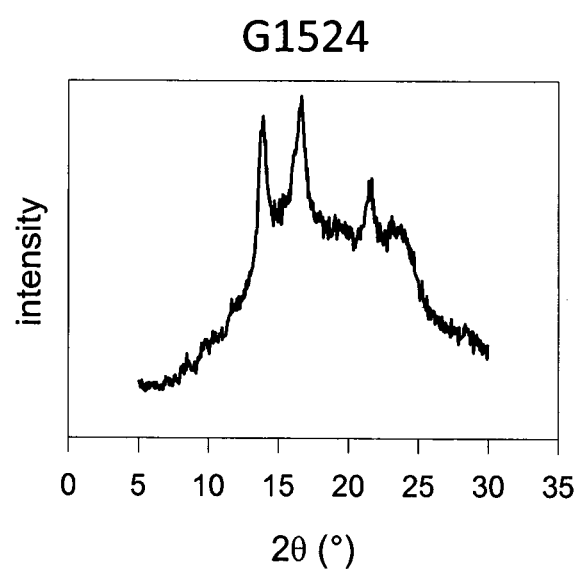
FIG. 13 shows the X-ray spectrum of the syndiotactic 1,2-polybutadiene obtained in Example 11.

FIG. 13 shows the X-ray spectrum of the syndiotactic 1,2-polybutadiene obtained.

Example 12 (IP200/1)

2 ml of 1,3-butadiene, equal to approx. 1.4 g, were condensed at low temperature (−20° C.) in a 25 ml tube. 13.5 ml of toluene were then added and the temperature of the solution obtained in this manner was adjusted to +20° C. Methylaluminoxane (MAO) in a solution in toluene (0.063 ml; 1×10$^{-4}$ moles, equal to approx. 5.8 g) was then added, followed by the complex FeCl$_2$(L3) [sample MG212] (1.83 ml of suspension in toluene at a concentration of 2 mg/ml; 1×10$^{-5}$ moles, equal to approx. 3.65 mg) obtained as described in Example 6. The whole was left to stand, under magnetic stirring, at +20° C., for 45 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 14:
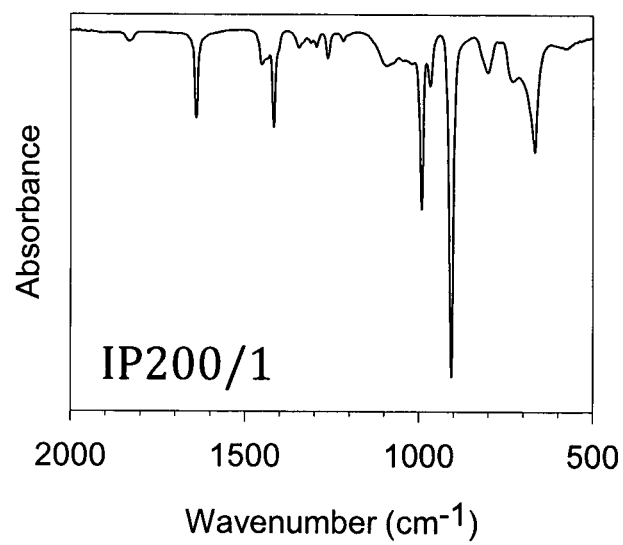
FIG. 14 shows the FT-IR spectrum of the syndiotactic 1,2-polybutadiene obtained in Example 12.

FIG. 14 shows the FT-IR spectrum of the syndiotactic 1,2-polybutadiene obtained.

Example 13 (G1526)

2 ml of 1,3-butadiene, equal to approx. 1.4 g, were condensed at low temperature (−20° C.) in a 25 ml tube. 14.24 ml of toluene were then added and the temperature of the solution obtained in this manner was adjusted to +20° C. Methylaluminoxane (MAO) in a solution in toluene (0.063 ml; 1×10$^{-4}$ moles, equal to approx. 5.8 g) was then added, followed by the complex FeCl$_3$(L1) [sample MG87] (1.7 ml of suspension in toluene at a concentration of 2 mg/ml; 1×10$^{-5}$ moles, equal to approx. 3.4 mg) obtained as described in Example 5. The whole was left to stand, under magnetic stirring, at +20° C., for 45 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 15:
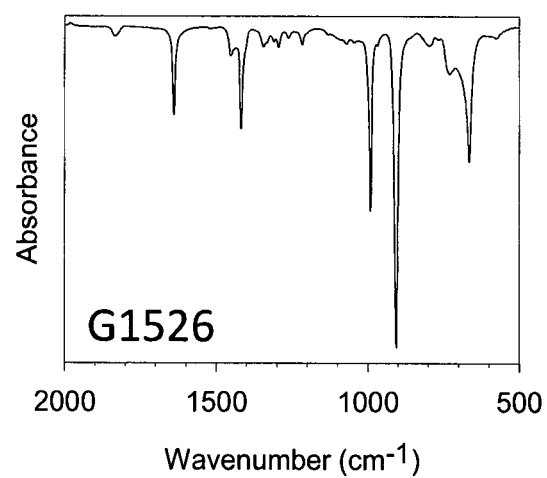
FIG. 15 shows the FT-IR spectrum of the syndiotactic 1,2-polybutadiene obtained in Example 13.

FIG. 15 shows the FT-IR spectrum of the syndiotactic 1,2-polybutadiene obtained.

Figure 16:
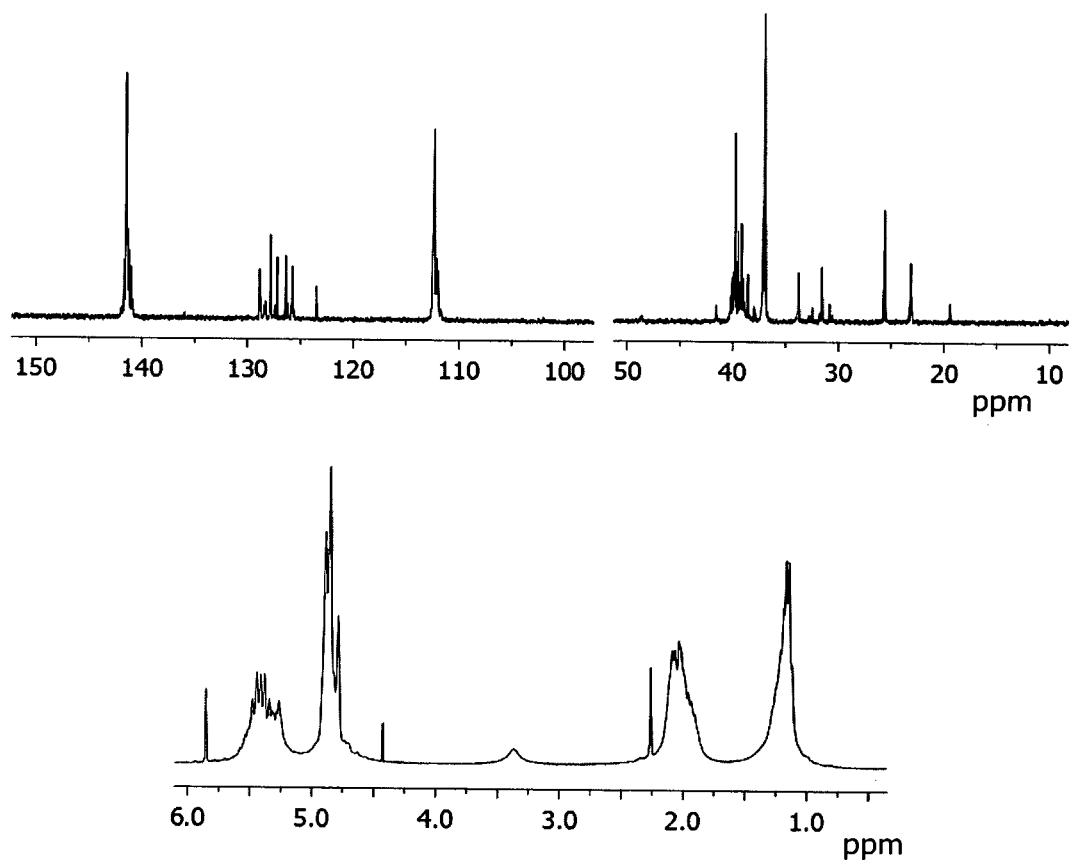
FIG. 16 shows the $^1$H-NMR (top) and $^{13}$C-NMR (bottom) spectra of the syndiotactic 1,2-polybutadiene obtained in Example 13.

FIG. 16 shows the $^1$H-NMR (top) and $^{13}$C-NMR (bottom) spectra of the syndiotactic 1,2-polybutadiene obtained.

Figure 17:
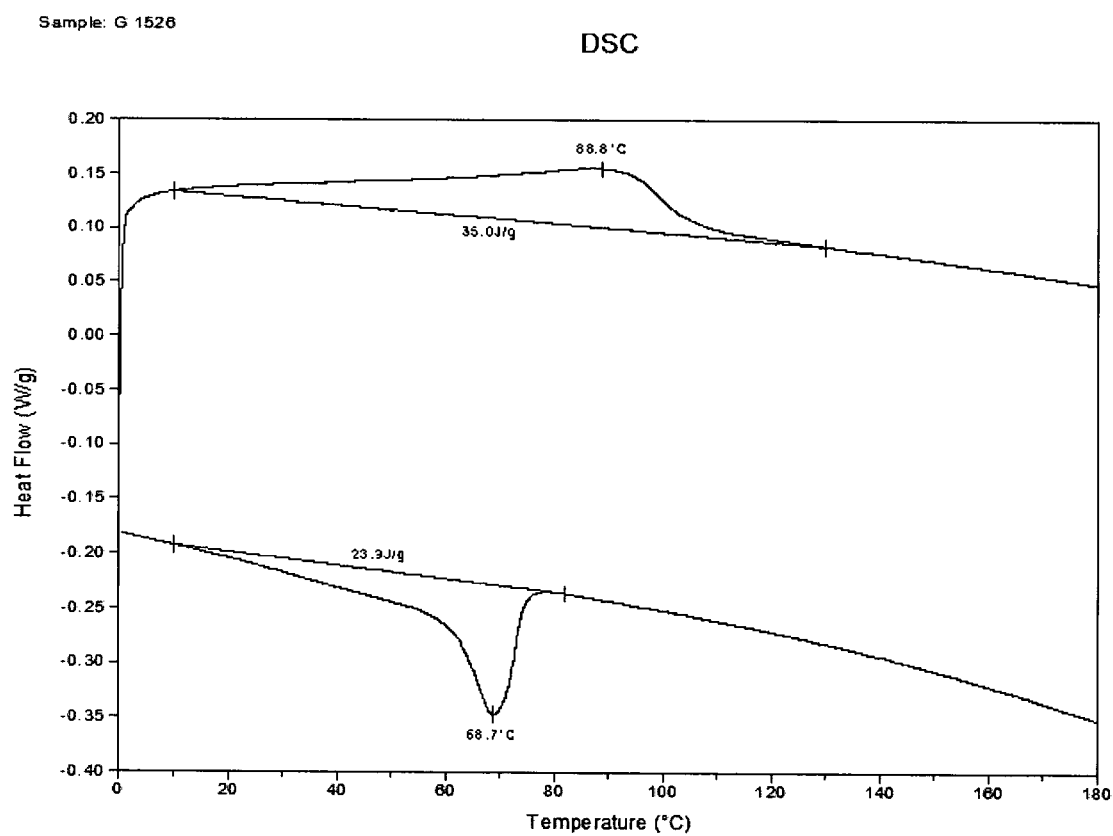
FIG. 17 shows the DSC curve of the syndiotactic 1,2-polybutadiene obtained in Example 13.

FIG. 17 shows the DSC curve of the syndiotactic 1,2-polybutadiene obtained.

Example 14 (G1526/1)

2 ml of 1,3-butadiene, equal to approx. 1.4 g, were condensed at low temperature (−20° C.) in a 25 ml tube. 14.24 ml of heptane were then added and the temperature of the solution obtained was adjusted to +20° C. Methylaluminoxane (MAO) in a solution in toluene (0.063 ml; 1×10$^{-4}$ moles, equal to approx. 5.8 g) was then added, followed by the complex FeCl$_3$(L1) [sample MG87] (1.7 ml of suspension in toluene at a concentration of 2 mg/ml; 1×10$^{-5}$ moles, equal to approx. 3.4 mg) obtained as described in Example 5. The whole was left to stand, under magnetic stirring, at +20° C. for 35 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 18:
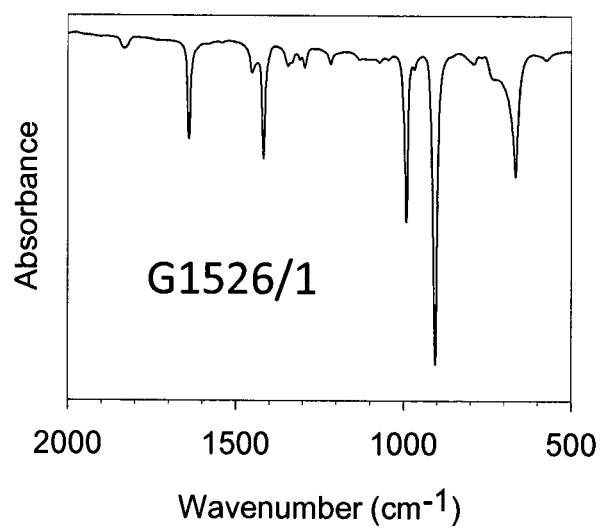
FIG. 18 shows the FT-IR spectrum of the syndiotactic 1,2-polybutadiene obtained in Example 14.

FIG. 18 shows the FT-IR spectrum of the syndiotactic 1,2-polybutadiene obtained.

Figure 19:
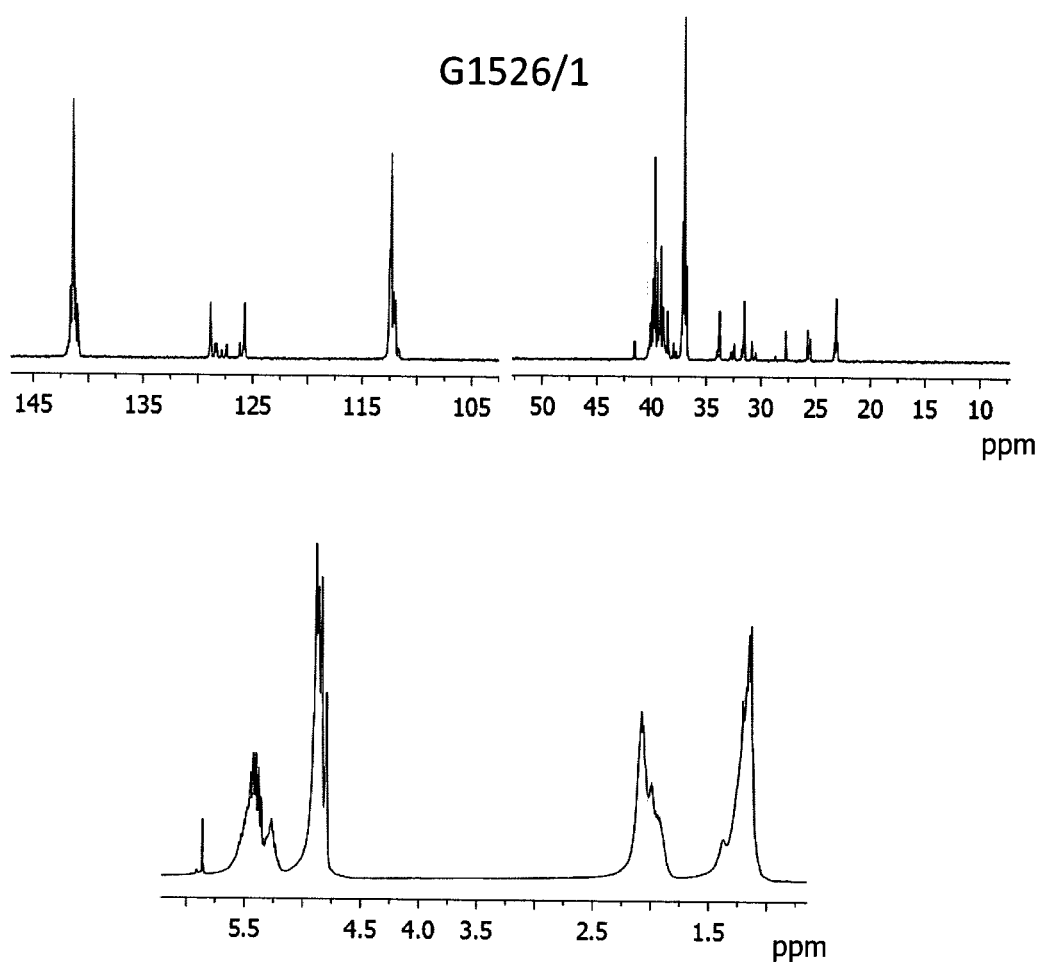
FIG. 19 shows the $^1$H-NMR (top) and $^{13}$C-NMR (bottom) spectra of the syndiotactic 1,2-polybutadiene obtained in Example 14.

FIG. 19 shows the $^1$H-NMR (top) and $^{13}$C-NMR (bottom) spectra of the syndiotactic 1,2-polybutadiene obtained.

Figure 20:
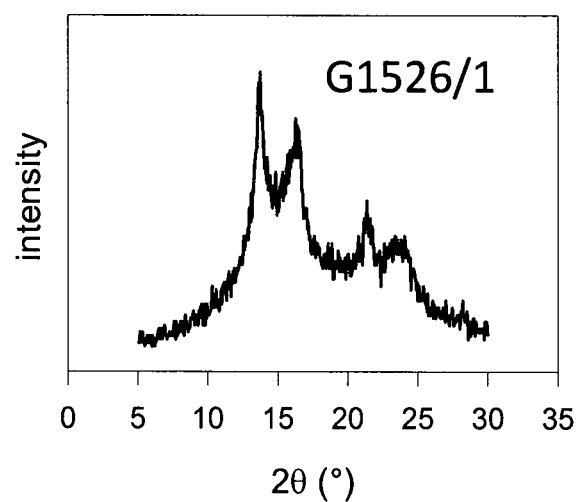
FIG. 20 shows the X-ray spectrum of the syndiotactic 1,2-polybutadiene obtained in Example 14.

FIG. 20 shows the X-ray spectrum of the syndiotactic 1,2-polybutadiene obtained.

Example 15 (G1523)

2 ml of 1,3-butadiene, equal to approx. 1.4 g, were condensed at low temperature (−20° C.) in a 25 ml tube. 14.08 ml of toluene were then added and the temperature of the solution obtained in this manner was adjusted to +20° C. Methylaluminoxane (MAO) in a solution in toluene (0.063 ml; 1×10$^{-4}$ moles, equal to approx. 5.8 g) was then added, followed by the complex FeCl$_3$(L2) [sample MG213] (1.86 ml of suspension in toluene at a concentration of 2 mg/ml; 1×10$^{-5}$ moles, equal to approx. 3.72 mg) obtained as described in Example 6. The whole was left to stand, under magnetic stirring, at +20° C., for 45 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 21:
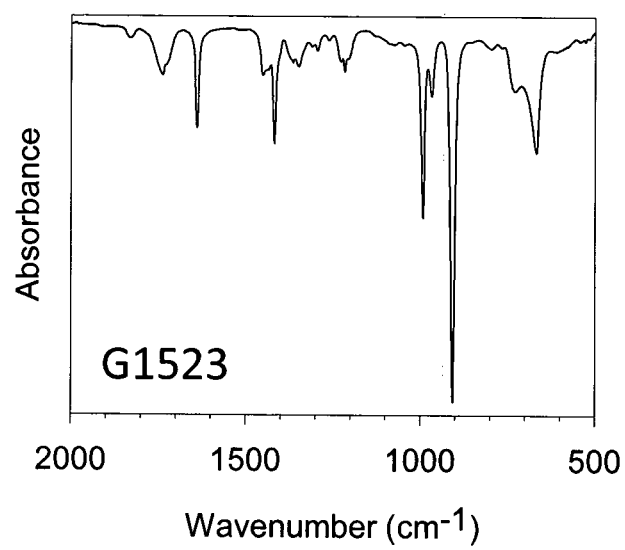
FIG. 21 shows the FT-IR spectrum of the syndiotactic 1,2-polybutadiene obtained in Example 15.

FIG. 21 shows the FT-IR spectrum of the syndiotactic 1,2-polybutadiene obtained.

Figure 22:
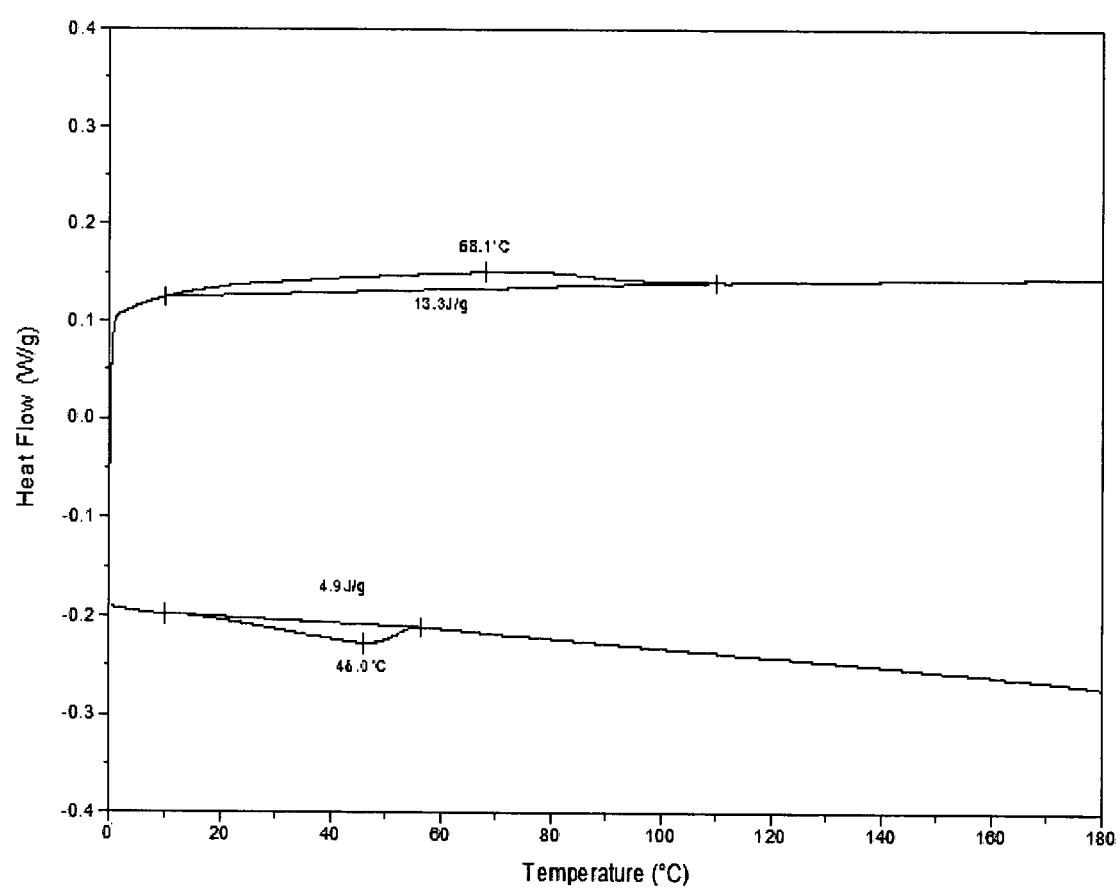
FIG. 22 shows the DSC curve of the syndiotactic 1,2-polybutadiene obtained in Example 15.

FIG. 22 shows the DSC curve of the syndiotactic 1,2-polybutadiene obtained.

Example 16 (G1523/1)

2 ml of 1,3-butadiene, equal to approx. 1.4 g, were condensed at low temperature (−20° C.) in a 25 ml tube. 14.08 ml of heptane were then added and the temperature of the solution obtained was adjusted to +20° C. Methylaluminoxane (MAO) in a solution in toluene (0.063 ml; 1×10$^{-4}$ moles, equal to approx. 5.8 g) was then added, followed by the complex FeCl$_3$(L2) [sample MG213] (1.86 ml of suspension in toluene at a concentration of 2 mg/ml; 1×10$^{-5}$ moles, equal to approx. 3.72 mg) obtained as described in Example 6. The whole was left to stand, under magnetic stirring, at +20° C., for 35 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 23:
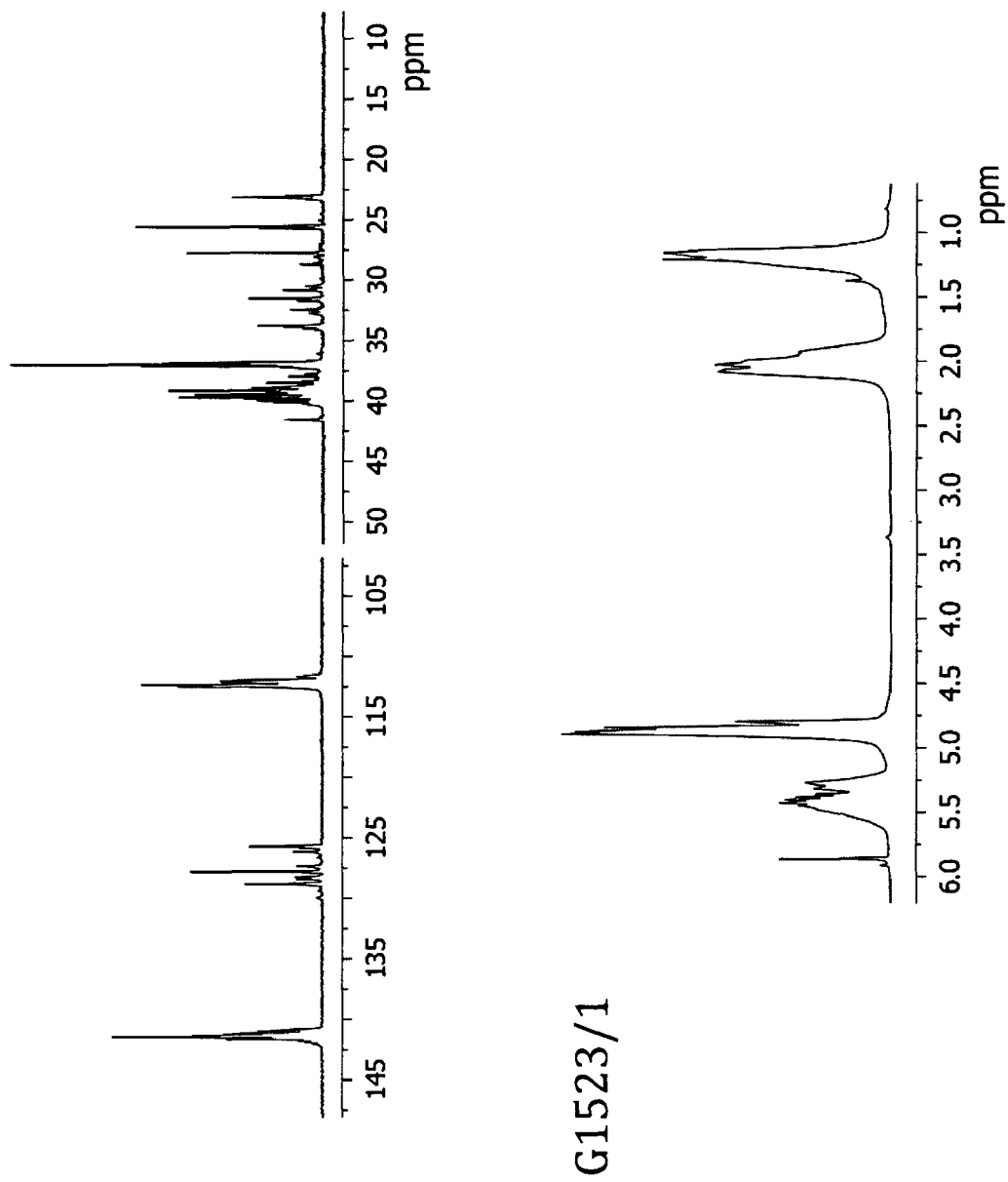
FIG. 23 shows the $^1$H-NMR (top) and $^{13}$NMR (bottom) spectra of the syndiotactic 1,2-polybutadiene obtained in Example 16.

FIG. 23 shows the $^1$H-NMR (top) and $^{13}$C-NMR (bottom) spectra of the syndiotactic 1,2-polybutadiene obtained.

Example 17 (IP204/1)

2 ml of 1,3-butadiene, equal to approx. 1.4 g, were condensed at low temperature (−20° C.) in a 25 ml tube. 13.4 ml of heptane were then added and the temperature of the solution obtained was adjusted to +20° C. Methylaluminoxane (MAO) in a solution in toluene (0.063 ml; 1×10$^{-4}$ moles, equal to approx. 5.8 g) was then added, followed by the complex FeCl$_3$(L3) [sample MG208] (2 ml of suspension in toluene at a concentration of 2 mg/ml; 1×10$^{-5}$ moles, equal to approx. 4 mg) obtained as described in Example 9. The whole was left to stand, under magnetic stirring, at +20° C., for 30 minutes. Polymerisation was then quenched by adding 2 ml of methanol containing a few drops of hydrochloric acid. The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 24:
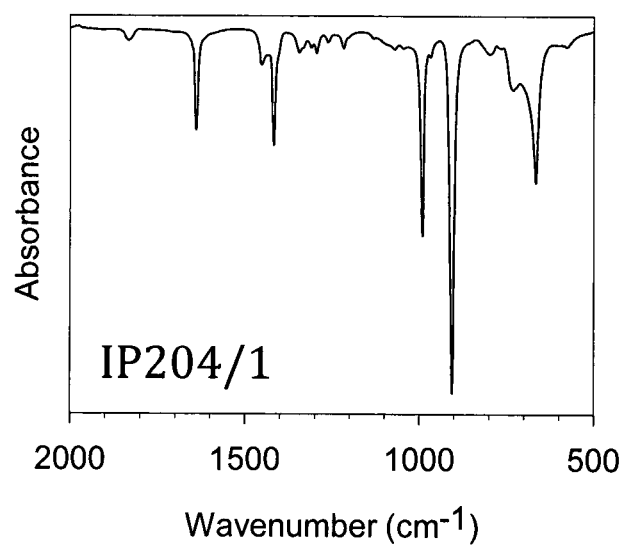
FIG. 24 shows the FT-IR spectrum of the syndiotactic 1,2-polybutadiene obtained in Example 17.

FIG. 24 shows the FT-IR spectrum of the syndiotactic 1,2-polybutadiene obtained.

Example 18

Synthesis of CoCl$_2$(PPh$_3$)$_2$

A solution of di-triphenylphosphine (6.08 g, 2.32×10$^{-2}$ moles) in ethanol (70 ml), was added, dropwise, under stirring, to a solution of anhydrous cobalt dichloride (CoCl$_2$) (1.30 g, 1×10$^{-2}$ moles) in ethanol (70 ml), in a 200 ml reaction flask, a pale blue suspension being formed. The suspension obtained was left to stand, under stirring, at room temperature, for 24 hours, and subsequently dried under vacuum at room temperature. The residue obtained was placed onto the filter of a heated extractor for solids, and extracted continuously with pentane, in such a manner as to remove any excess phosphine: extraction in toluene was then continued for a further 24 hours, blue crystals being obtained. The blue crystals obtained were separated by siphoning off the supernatant solution and further crystals were obtained by cooling the siphoned off solution. Said crystals were then dried under vacuum, at room temperature, 4.58 g of a light blue solid product corresponding to the phosphine complex CoCl$_2$(PPh$_3$)$_2$ and amounting to conversion of 70% based on the anhydrous cobalt dichloride (CoCl$_2$), being obtained.

Elemental analysis [found (calculated)]: Co: 9.10% (9.01%); Cl: 10.80% (10.84%); P: 9.40% (9.47%); C: 66.20% (66.07%); H: 4.70% (4.62%).

Example 19 (G1528) (Comparative)

2 ml of 1,3-butadiene, equal to approx. 1.4 g, were condensed at low temperature (−20° C.) in a 25 ml tube. 12.4 ml of toluene were then added and the temperature of the solution obtained in this manner was adjusted to +25° C. Methylaluminoxane (MAO) in a solution in toluene (0.63 ml; 1×10$^{-3}$ moles, equal to approx. 58 g) was then added, followed by the complex CoCl$_2$(PPh$_3$)$_2$(2.96 ml of suspension in toluene at a concentration of 2 mg/ml; 1×10$^{-5}$ moles, equal to approx. 5.92 mg) obtained as described in Example 11. The whole was left to stand, under magnetic stirring, at +25° C., for 40 minutes. Polymerisation was then quenched by adding 2 ml of methanol containing a few drops of hydrochloric acid.

The polymer obtained was then coagulated by adding 40 ml of a methanolic solution containing 4% Irganox® 1076 (Ciba) antioxidant, 1.4 g of syndiotactic 1,2-polybutadiene being obtained: further characteristics of the process and of the syndiotactic 1,2-polybutadiene obtained are shown in Table 1.

Figure 25:
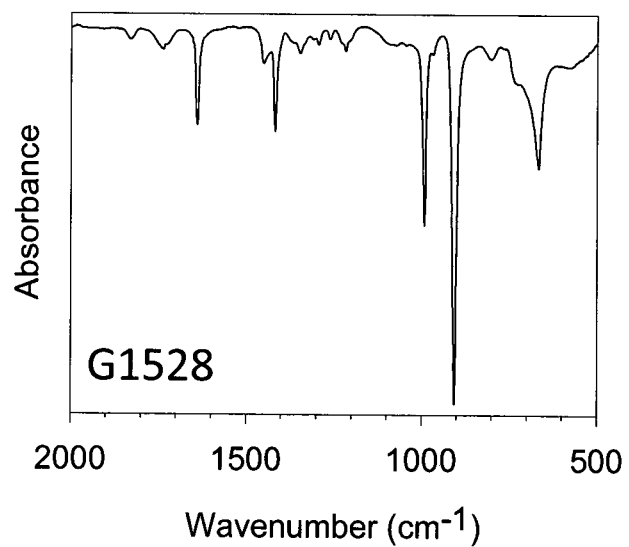
FIG. 25 shows the FT-IR spectrum of the syndiotactic 1,2-polybutadiene obtained in Example 19.

FIG. 25 shows the FT-IR spectrum of the syndiotactic 1,2-polybutadiene obtained.

Figure 26:
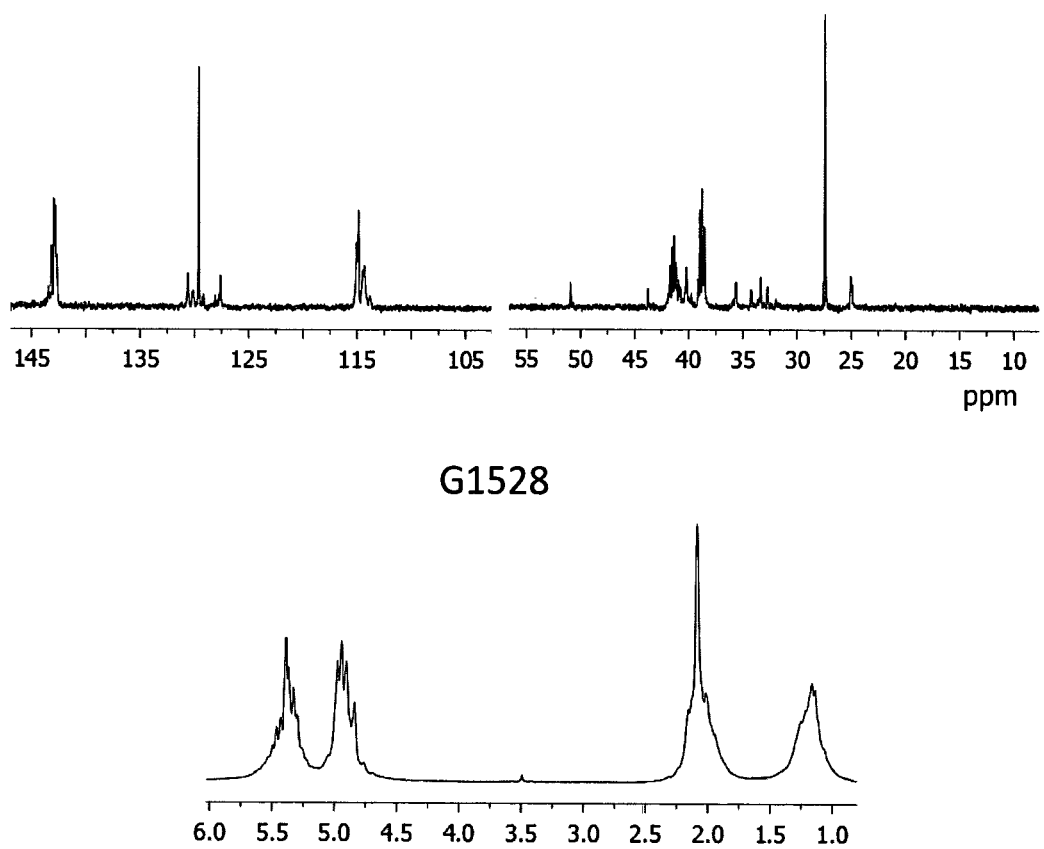
FIG. 26 shows the $^1$H-NMR (top) and $^{13}$C-NMR (bottom) spectra of the syndiotactic 1,2-polybutadiene obtained in Example 19.

FIG. 26 shows the $^1$H-NMR (top) and $^{13}$C-NMR (bottom) spectra of the syndiotactic 1,2-polybutadiene obtained.

Figure 27:
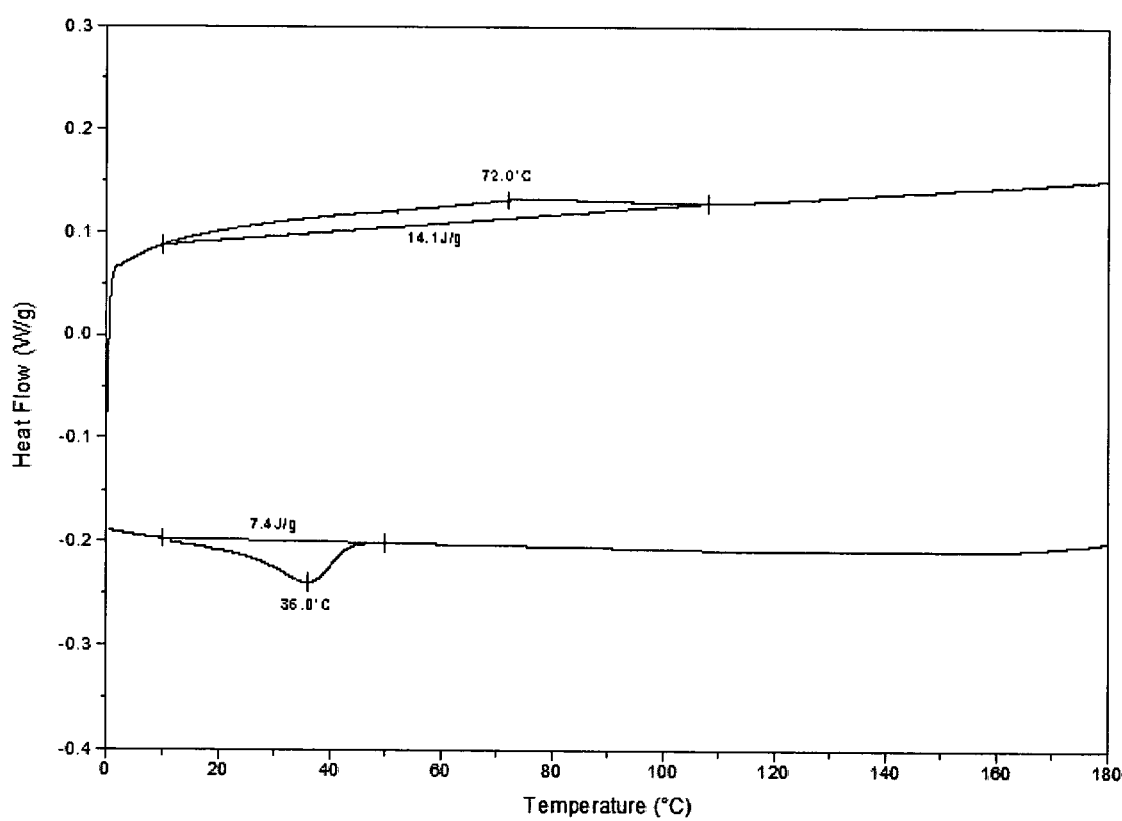
FIG. 27 shows the DSC curve of the syndiotactic 1,2-polybutadiene obtained in Example 19.

FIG. 27 shows the DSC curve of the syndiotactic 1,2-polybutadiene obtained.

Figure 28:
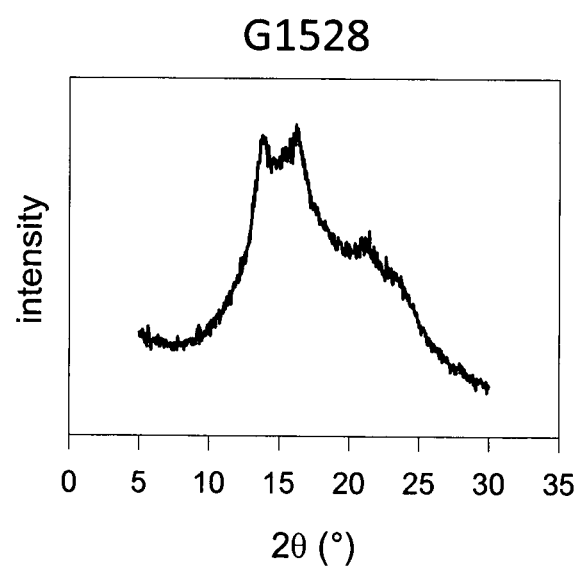
FIG. 28 shows the X-ray spectrum of the syndiotactic 1,2-polybutadiene obtained in Example 19.

FIG. 28 shows the X-ray spectrum of the syndiotactic 1,2-polybutadiene obtained.

It is apparent from the data shown in Table 1 that the syndiotactic 1,2-polybutadiene obtained in accordance with the process provided by the present invention (Examples 10-17) exhibits characteristics similar to those of the syndiotactic 1,2-polybutadiene obtained with a process known in the art using a catalytic system based on cobalt (Example 19).

The invention claimed is:

1. Process for the preparation of syndiotactic 1,2-polybutadiene comprising polymerising 1,3-butadiene in the presence of a catalytic system comprising:
at least one pyridyl iron complex having the general formula (I):

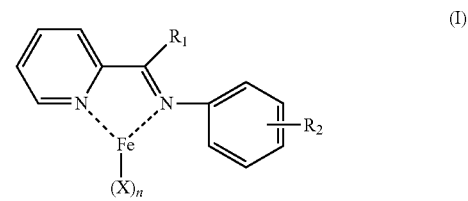

in which:
R$_1$ represents a hydrogen atom; or a methyl group;
R$_2$ represents a hydrogen atom; or is selected from linear or branched C$_1$-C$_{10}$ alkyl groups;
X, identical or different to one another, represent a halogen atom; or are selected from linear or branched, C$_1$-C$_{20}$ alkyl groups, —OCOR$_3$ groups or —OR$_3$ groups in which R$_3$ is selected from linear or branched C$_1$-C$_{20}$ alkyl groups;
n is 2 or 3;
at least one aluminoxane having the general formula (II):

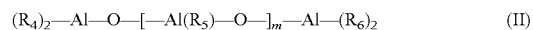

in which R$_4$, R$_5$ and R$_6$, identical or different to one another, represent a hydrogen atom, or a halogen atom; or are selected from linear or branched C$_1$-C$_{20}$ alkyl groups, cycloalkyl groups, aryl groups, said groups being optionally substituted with one or more silicon atoms or germanium; and m is an integer ranging from 0 to 1000;
in which the molar ratio between the aluminium present in the aluminoxane having the general formula (II) and the iron present in the pyridyl iron complex having the general formula (I) is ranging from 5 to 20.

2. Process for the preparation of syndiotactic 1,2-polybutadiene according to claim 1, in which in said pyridyl iron complex having the general formula (I):
R$_1$ represents a hydrogen atom; or a methyl group;
R$_2$ represents a hydrogen atom; or a methyl group, an ethyl group, an n-propyl group, an iso-propyl group;
X, identical to one another, represent a halogen atom selected from chlorine, bromine, iodine;
n is 2 or 3.

TABLE 1

Polymerisation of 1,3-butadiene with catalytic systems comprising pyridyl iron complexes

| Example | Al/Fe (molar ratio) | Time (min) | Conversion (%) | 1,4-cis (%) | 1,2 (%) | (rr %) | M$_w$ (g × mol$^{-1}$) | M$_w$/M$_n$ | T$_m$ (° C.) | T$_c$ (° C.) |
|---|---|---|---|---|---|---|---|---|---|---|
| 10 | 10 | 45 | 100 | 16 | 84 | 69.7 | 355000 | 1.9 | 102.3 | 78.0 |
| 11 | 10 | 45 | 100 | 24 | 76 | 60.4 | 350000 | 2.0 | 80.9 | 59.1 |
| 12 | 10 | 30 | 100 | 22 | 78 | 66.8 | 377000 | 1.9 | 87.0 | 68.5 |
| 13 | 10 | 45 | 100 | 20 | 80 | 68.4 | 349000 | 2.3 | 88.8 | 68.7 |
| 14 | 10 | 35 | 100 | 15 | 85 | 70.4 | 337500 | 2.1 | 110.2 | 82.7 |
| 15 | 10 | 45 | 100 | 29 | 71 | 54.9 | 344000 | 1.9 | 68.1 | 46.0 |
| 16 | 10 | 35 | 100 | 22 | 78 | 58.1 | 333000 | 1.8 | 78.3 | 55.7 |
| 17 | 10 | 30 | 100 | 20 | 82 | 71.5 | 369000 | 1.8 | 106.6 | 79.9 |
| 19(*) | 100 | 40 | 100 | 28 | 72 | 55.1 | 317000 | 1.9 | 72.0 | 36.0 |

(*)comparative

3. Process for the preparation of syndiotactic 1,2-polybutadiene according to claim 1, in which said aluminoxane having the general formula (II) is selected from: methylaluminoxane (MAO), ethylaluminoxane, n-butylaluminoxane, tetra-iso-butylaluminoxane (TIBAO), tert-butylaluminoxane, tetra-(2,4,4-trimethylpentyl)aluminoxane (TIOAO), tetra-(2,3-dimethylbutyl)aluminoxane (TDMBAO), tetra-(2,3,3-trimethylbutyl)aluminoxane (TTMBAO), or mixtures thereof.

4. Process for the preparation of syndiotactic 1,2-polybutadiene according to claim 1 in which:
said process is carried out in the presence of at least one inert organic solvent selected from: saturated aliphatic hydrocarbons selected from butane, pentane, hexane, heptane, or mixtures thereof; saturated cycloaliphatic hydrocarbons selected from cyclopentane, cyclohexane, or mixtures thereof; mono-olefins selected from 1-butene, 2-butene, or mixtures thereof; aromatic hydrocarbons selected from benzene, toluene, xylene, or mixtures thereof; halogenated hydrocarbons selected from methylene chloride, chloroform, carbon tetrachloride, trichloroethylene, perchloroethylene, 1,2-dichloroethane, chlorobenzene, bromobenzene, chlorotoluene, or mixtures thereof; and/or
in said process the concentration of 1,3-butadiene in said inert organic solvent is ranging from 5% by weight to 50% by weight, based on the total weight of the 1,3-butadiene/inert organic solvent mixture; and/or
said process is carried out at a temperature ranging from −30° C. to +60° C.

5. Shoe soles comprising the syndiotactic 1,2-polybutadiene obtained by the process according to claim 1.

6. Process for the preparation of syndiotactic 1,2-polybutadiene according to claim 1,
in which in said pyridyl iron complex having the general formula (I):
$R_1$ represents a hydrogen atom; or a methyl group;
$R_2$ represents a hydrogen atom; or a methyl group or an iso-propyl group;
X, identical to one another, represent a chlorine atom;
n is 2 or 3.

* * * * *